(12) United States Patent
McKee et al.

(10) Patent No.: US 9,895,693 B2
(45) Date of Patent: Feb. 20, 2018

(54) AUTOMATED BLOTTING USING SLIDING DEVICES

(71) Applicant: Bio-Rad Laboratories, Inc., Hercules, CA (US)

(72) Inventors: Clayton T. McKee, Davis, CA (US); William Strong, El Cerrito, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 169 days.

(21) Appl. No.: 14/642,487

(22) Filed: Mar. 9, 2015

(65) Prior Publication Data

US 2015/0253251 A1    Sep. 10, 2015

Related U.S. Application Data

(60) Provisional application No. 62/067,915, filed on Oct. 23, 2014, provisional application No. 61/949,632, filed on Mar. 7, 2014.

(51) Int. Cl.
*G01N 33/543* (2006.01)
*B01L 3/00* (2006.01)
(Continued)

(52) U.S. Cl.
CPC ...... *B01L 3/502738* (2013.01); *C12Q 1/6806* (2013.01); *G01N 27/44717* (2013.01);
(Continued)

(58) Field of Classification Search
None
See application file for complete search history.

(56) References Cited

U.S. PATENT DOCUMENTS

2003/0019817 A1    1/2003  Thomas et al.
2012/0028342 A1    2/2012  Ismagilov et al.
(Continued)

FOREIGN PATENT DOCUMENTS

WO    2013/158827 A1    10/2013

OTHER PUBLICATIONS

International Search Report and Written Opinion from PCT/US2015/019495, dated Jul. 9, 2015.
(Continued)

*Primary Examiner* — Rebecca L Martinez
(74) *Attorney, Agent, or Firm* — Kilpatrick Townsend and Stockton LLP

(57) ABSTRACT

Devices, systems, methods, and kits are provided for performing separation, immobilization, blotting, and/or detection of analytes from biological samples. In some embodiments, the devices are constructed from two solid substrates with surfaces in contact. The devices include a plurality of channels formed from indentations in these surfaces. The indentations can be aligned with each other across the interface between the substrates, and realigned by shifting or sliding one substrate relative to the other. In some embodiments, the devices are constructed from three layers of a solid substrate. A separation channel in the middle layer of the device is first used for analyte separation. The middle layer can then be slid relative the top and/or bottom layer, thereby aligning the separation channel with a blotting membrane. Analytes can then be transferred to the membrane using electrodes in the top and bottom layers.

20 Claims, 14 Drawing Sheets

(51) Int. Cl.
*G01N 27/447* (2006.01)
*C12Q 1/68* (2018.01)

(52) U.S. Cl.
CPC . *G01N 27/44739* (2013.01); *G01N 33/54366* (2013.01); *B01L 2200/0605* (2013.01); *B01L 2200/0642* (2013.01); *B01L 2300/045* (2013.01); *B01L 2300/047* (2013.01); *B01L 2300/0816* (2013.01); *B01L 2300/0874* (2013.01); *B01L 2400/0415* (2013.01); *B01L 2400/0418* (2013.01); *B01L 2400/0421* (2013.01); *B01L 2400/0487* (2013.01); *B01L 2400/065* (2013.01)

(56) References Cited

U.S. PATENT DOCUMENTS

| | | |
|---|---|---|
| 2012/0213667 A1 | 8/2012 | Roach et al. |
| 2013/0130275 A1* | 5/2013 | Yoshimura ............. G01N 33/86 435/7.4 |
| 2013/0213811 A1 | 8/2013 | Kennedy et al. |
| 2013/0281316 A1 | 10/2013 | Ismagilov et al. |

OTHER PUBLICATIONS

Partial European Search Report from EP Appl. No. 15758608.2, dated Nov. 28, 2016.

\* cited by examiner

Top Half-Space

Bottom Half-Space

Covalently attach proteins, remove excess matrix and then translate top half-space to create a new channel In a newly created channel, conduct a Western blot immunoassay and then image result.

Protein Separation Channel (PSC) (separate and immobilize proteins, then translate to bring PSC to PDC)

Protein Detection Channel (PDC)

Flow Ab's in protein detection channel.

Buffer & Sample Ports    Protein Separation Channels    Ab Probing Channels

Cross-section view of chip. Example of an 8 channel design. Empty spaces between lanes for multiplex Ab probing, after chip translation Vacuum fill channels with matrix Load and separate proteins then cross-link to walls After chip translation, one half of each lane can be probed with a different Ab. Vacuum fill channels with wash, block, primary, secondary.

Detect targets optically through chip.

After protein capture, rotate chip to align protein separate channel with Ab probe channels Load sample in 12 ports, lower anodes onto device, separate proteins and then crosslink to wall Vacuum fill all 12 separation channels with block, primary and secondary solutions

Fractionation + ELISA

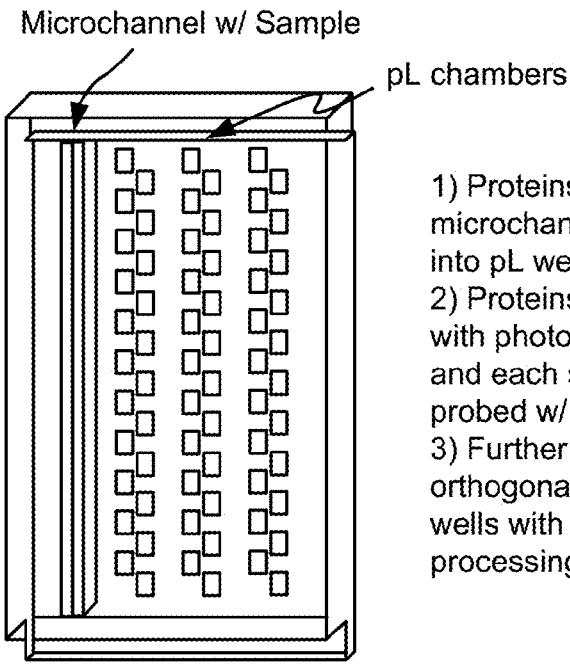

1) Proteins separated in microchannel and then fractionated into pL wells by translating plates.
2) Proteins are captured to wells with photocrosslinker and probed and each set of pico chambers probed w/ different antibody.
3) Further translation of chip in orthogonal direction could cover wells with channel for immuno-processing steps.

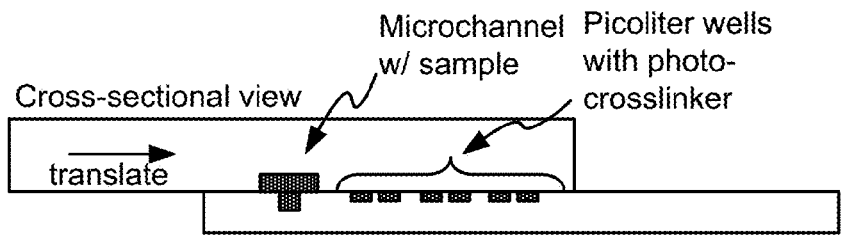

*FIG. 7C*

After translation of plates, separated proteins are fractionated/dosed into discrete pL wells for capture and antibody probing.

AUTOMATED BLOTTING USING SLIDING DEVICES

CROSS-REFERENCES TO RELATED APPLICATIONS

The present application claims priority to U.S. Provisional Application No. 61/949,632 entitled "MICRO FLUIDIC WESTERN BLOT" and filed Mar. 7, 2014, as well as to U.S. Provisional Application No. 62/067,915 entitled "AUTOMATED BLOTTING USING SLIDING DEVICE WITH INTEGRATED MEMBRANE" and filed Oct. 23, 2014. The entire contents of each priority application are incorporated herein by reference for all purposes.

BACKGROUND OF THE INVENTION

Electroblotting is a widely used technique in biotechnology. The technique involves applying a potential difference across a matrix in which charged analytes, such as DNA, RNA, or protein, are distributed. The potential difference causes the analytes to migrate out of the matrix and become deposited on a surface or 'blot' next to the matrix, where they are immobilized. The analytes can then be detected using fluorescence, chemiluminescence, radioactivity, or other phenomena, by probing the analytes with one or more detectable binding partners.

Electroblotting is often paired with, and performed immediately after, a technique such as electrophoresis that separates the analytes in the matrix on the basis of size or charge. Thus, electroblotting provides a way to interrogate a biological sample on the basis of characteristics orthogonal or complementary to those accessible by electrophoresis. For example, a protein sample can be subjected to electrophoresis in a polyacrylamide gel and then transferred to a nitrocellulose membrane by electroblotting. The migration rates of proteins in the gel can reflect their molecular weights, and the affinities of these proteins for binding partners on the membrane can reflect whether the proteins contain certain sequence motifs. Because electroblotting follows electrophoresis and can preserve the separation of analytes achieved by electrophoresis, detection of analytes on a blot can reveal multiple levels of information about the sample from which the analytes originate.

Various kinds of electroblotting are known and practiced in the art. When the analytes are DNA fragments, the transfer of the analytes out of a gel or other matrix and onto a blot is called Southern blotting after its originator, the British biologist Edwin M. Southern. By analogy, the transfer of RNA fragments is termed northern blotting, and the transfer of proteins or polypeptides is termed western blotting. Still further examples are "eastern" blots for post-translational modifications, and "far western" blots for protein interactions. Some of these blotting techniques can be performed in the absence of an applied potential difference, with the transfer of analytes from the matrix to the blot instead driven by capillary action.

To carry out electroblotting as it is typically practiced, a complex procedure is required. After separating analytes in the matrix, such as by electrophoresis, the matrix and blot must be precisely juxtaposed to facilitate the transfer of analytes. Next, electrodes and other apparatus must be assembled around the matrix and blot. The apparatus can include a buffer reservoir, sponges, or wetted paper to allow current to flow between the electrodes. A potential difference is then applied between the electrodes and transfer occurs.

Before analytes can be detected, however, the apparatus must be disassembled and the blot must be removed from the matrix and handled further. The handling is required to expose analytes of interest on the blot to binding partners in a controlled manner. For example, in the case of western blotting, the blot may be incubated with a blocking protein that binds the blot non-specifically, a primary antibody that binds specifically to an analyte of interest, and a labeled secondary antibody that binds to the primary antibody. Each of these incubations requires submerging the blot in a different solution. Detection then can involve placing the blot next to a piece of film or an optical scanner sensitive to a label on one of the binding partners.

The electroblotting procedure is costly on several levels. The procedure is time consuming, in some cases taking place over the course of several days, and is not easily automated. The blot must be mechanically manipulated in several different ways, and these manipulations require care to ensure, for example, that the matrix and blot do not break, or that the blot does not come into contact with contaminants. Thus, the procedure requires a highly skilled, extensively trained practitioner to execute successfully. Electroblotting is also costly in terms of reagents. The blot is often incubated with a large excess of binding partners in order to detect analytes with adequate sensitivity, even though these analytes may occupy only a small portion of the surface area of the blot.

Electroblotting also does not always yield reproducible or quantitative data. Variability in sample size, transfer efficiency, and the affinities of binding partners for analytes can result in insensitive or imprecise detection. The same analyte may not be detectable at the same level from one electroblotting procedure to the next, and differences in the signals arising from the analyte in separate procedures may not reflect differences in the abundance or integrity of the analyte. Similarly, the signals arising from two different analytes in the same procedure may not accurately reflect the relative concentrations of these analytes. In addition, many electroblotting procedures allow detection of only a subset of the analytes present in the sample, and preclude detection of analytes on the matrix. Thus, information about the composition of the sample (for example, the distribution of protein molecular weights) can be lost upon transferring analytes from the matrix to the blot.

BRIEF SUMMARY OF THE INVENTION

Provided herein are devices, methods, systems, and kits for separating, immobilizing, blotting, and/or detecting analytes of one or more biological samples.

In a first aspect of the invention, a device is provided for separating and detecting analytes of a biological sample. The device includes: a first solid substrate comprising a first surface, a plurality of $\alpha$ first half-spaces, and a plurality of $\beta$ first half-spaces, the $\alpha$ and $\beta$ first half-spaces disposed in the first surface in a repeating array, such that each $\alpha$ first half-space is adjacent to a $\beta$ first half-space; a first capture agent disposed on the first surface within the $\alpha$ first half-spaces; a second solid substrate comprising a second surface, a plurality of $\alpha$ second half-spaces and a plurality of $\beta$ second half-spaces, the $\alpha$ and $\beta$ second half-spaces disposed in the second surface in a repeating array, such that each $\alpha$ second half-space is adjacent to a $\beta$ second half-space; a second capture agent disposed on the second surface within the $\alpha$ second half-spaces; and a plurality of access ports.

In the device, the first surface and second surface contact each other at an interface. The half-spaces are configured to contain fluids or separation media. The first half-spaces are complementary in shape to the second half-spaces, such that, when one first half-space is aligned with one second half-space, the one first half-space and the one second half-space together form a channel. The first solid substrate is configured to alternatively occupy two positions relative to the second solid substrate, the two positions being: an α-α position, such that the α first half-spaces are aligned with α second half-spaces to form separation channels, and an α-β position, such that the α first half-spaces are aligned with β second half-spaces to form α-β channels, and the β first half-spaces are aligned with α second half-spaces to form β-α channels, the α-β and β-α channels being detection channels. The first solid substrate is configured to slide past the second solid substrate along the interface. The access ports are configured to provide access to the separation channels and the detection channels from space outside the device.

In some embodiments of the device, the first capture agent and the second capture agent are the same. In some embodiments, the first capture agent and the second capture agent are different. In some embodiments, the first capture agent or the second capture agent is a crosslinker, such as benzophenone, formaldehyde, or glutaraldehyde. In some embodiments, the first capture agent or the second capture agent is an affinity structure, such as a protein or nucleic acid. In some embodiments, the first capture agent is attached to the first surface through a linker, or the second capture agent is attached to the second surface through a linker.

In some embodiments of the device, the first surface and the second surface are configured to contact each other with a fluid-tight seal, such that a fluid contained in an α first half-space, a β first half-space, an α second half-space, a β second half-space, a separation channel, or a detection channel cannot escape from said half-space or channel through the interface.

In some embodiments of the device, the access ports comprise through-holes in the first solid substrate, and at least one through-hole provides a passage between each α first half-space and space outside the first solid substrate. In these embodiments: A vacuum source or pressure source can be coupled to at least one of the through-holes. An electrode can be disposed in at least one of the through-holes. Two through-holes can provide passages between each α first half-space and space outside the first solid substrate, the two through-holes occurring at opposite ends of the α first half-space. An electrode can be disposed in each of these two through-holes. A plurality of through-holes can provide passages between each α first half-space and space outside the first solid substrate, wherein at least one of the plurality of through-holes is coupled to a vacuum source or pressure source, an electrode is disposed in at least one of the plurality of through-holes, and the at least one through-hole coupled to the vacuum source or pressure source and the at least one through-hole in which an electrode is disposed occur at the same end of the α first half-space. At least one through-hole can provide a passage between each β first half-space and space outside the first solid substrate. Two through-holes can provide passages between each β first half-space and space outside the first solid substrate, the two through-holes occurring at opposite ends of the β first half-space. The access ports can further comprise through-holes in the second solid substrate, and at least one through-hole can provide a passage between each α second half-space and space outside the second solid substrate.

In some embodiments of the device, the access ports are configured for introducing fluids or separation media to the separation channels and the detection channels. In some embodiments, the access ports are configured for removing fluids or separation media from the separation channels and the detection channels. In some embodiments, the access ports are configured for supplying electrical current to opposite ends of the separation channels.

In some embodiments, the first solid substrate or the second solid substrate is transparent, in whole or in part, to UV and/or visible light. In some embodiments, the device further comprises a UV and/or visible light source configured to direct light into the separation channels or the detection channels. In some embodiments, the device further comprises a detector configured to detect light emitted from the detection channels.

In some embodiments of the device, the first half-spaces and second half-spaces are linear. In these embodiments: The α first half-spaces and the β first half-spaces can be parallel to each other in the first surface. Each first half-space can be disposed along a separation axis, and the first solid substrate and second solid substrate can be configured to slide past each other such that the first solid substrate or the second solid substrate moves in a direction orthogonal to the separation axis. The first half-spaces can radiate from and terminate at a central location in the first solid substrate, and the first solid substrate can be configured to be rotated about the central location, thereby allowing the first solid substrate to slide past the second solid substrate. The device can further include an electrode disposed at the central location, or a vacuum source or a pressure source coupled to the central location.

In some embodiments of the device, the depth of at least one β first half-space is less than the depth of at least one α first half-space. In these embodiments: The depth of every β first half-space can be less than the depth of every α first half-space. The depth of at least one β first half-space can be about zero. The depth of at least one β second half-space can be less than the depth of at least one α second half-space. The depth of every β second half-space can be less than the depth of every α second half-space. The depth of at least one β second half-space can be about zero.

In some embodiments of the device, the β first half-spaces and the β second half-spaces have depths of about zero. In some embodiments, the α first half-spaces are about equal in depth to the β first half-spaces. In some embodiments, the α first half-spaces are about equal in depth to the α second half-spaces. In some embodiments, the α first half-spaces, the β first half-spaces, the α second half-spaces, and the β second half-spaces are all about equal in depth. In some embodiments, the first half-spaces have a first depth, the second half-spaces have a second depth, and the second depth is less than the first depth.

In the first aspect of the invention, a system is also provided for automatically separating and immobilizing analytes of a biological sample. The system includes the device described above, and a motor configured to drive the sliding movement of the first solid substrate past the second solid substrate, from the α-α position to the α-β position. In some embodiments, the system further includes a vacuum source or pressure source coupled to at least one of the access ports. In some embodiments, the system further includes a pair of electrodes disposed at opposite ends of a separation channel, wherein the electrodes are disposed in access ports. The system can also include a power supply configured to energize the electrodes to opposite polarities. In some embodiments, the system further includes a UV and/or visible light source configured to direct light into the separation channels or the detection channels. In some embodiments, the system further includes a detector configured to detect light emitted from the detection channels.

In the first aspect of the invention, a method of separating and detecting analytes of a biological sample, using the device described above, is also provided. The method includes: (a) separating analytes of the biological sample in a separation medium, wherein the separation medium is contained in a separation channel, and the separation channel is formed from an α first half-space aligned with an α second half-space; (b) immobilizing the analytes within the separation channel, using the first capture agent and the second capture agent; (c) sliding the first solid substrate past the second solid substrate, from the α-α position to the α-β position, thereby disrupting the separation channel and forming two detection channels, wherein one detection channel is an α-β channel formed from the α first half-space and the other detection channel is a β-α channel formed from the α second half-space; and (d) detecting the immobilized analytes in at least one of the two detection channels formed in step (c).

In some embodiments, the method further includes introducing the separation medium into the separation channel before step (a). The biological sample can be suspended in the separation medium before the separation medium is introduced into the separation channel. In some embodiments, the method further includes loading the biological sample into the separation medium. In some embodiments, separating the analytes comprises performing electrophoresis, electroosmosis, or isoelectric focusing. In some embodiments, the separation medium comprises a polymer solution, crosslinked polymer matrix, or hydrogel. The separation medium can comprise a polymer solution and the polymer solution can comprise dextran or agarose. The separation medium can comprise a crosslinked polymer matrix and the crosslinked polymer matrix can comprise polyacrylamide and bis-acrylamide.

In some embodiments of the method, the first capture agent or the second capture agent is a crosslinker, and immobilizing the analytes comprises crosslinking the analytes to the first surface or the second surface. The crosslinking can be effected by exposing the separation channel to UV light. In some embodiments, the first capture agent or the second capture agent is an affinity structure, and immobilizing the analytes comprises binding the analytes to the affinity structure.

Some embodiments of the method further include removing the separation medium from the separation channel or detection channels after step (b). In these embodiments, the separation medium can be removed from the detection channels after step (c). In some embodiments, the analytes are separated along a separation axis, and sliding the first solid substrate past the second solid substrate comprises moving the first solid substrate or the second solid substrate in a direction orthogonal to the separation axis.

Some embodiments of the method further include introducing a detection medium into the separation channel or the detection channels. The detection medium can be introduced into the separation channel before step (c), or introduced into the detection channels after step (c). These embodiments can further include removing the separation medium from the separation channel after step (b), wherein the separation medium is displaced by the detection medium. The detection medium can comprise a binding partner for one or more analytes. The binding partner can be a protein or nucleic acid, such as an antibody or a labeled nucleic acid probe. The detection medium can further comprise a reagent that binds to or reacts with the binding partner. The reagent can comprise a secondary antibody or a chemiluminescent substrate. The detection medium can also comprise a blocking agent.

In some embodiments of the method, detecting the immobilized analytes comprises detecting color, fluorescence, chemiluminescence, or radioactivity. In some embodiments, detecting the immobilized analytes comprises exposing the immobilized analytes in the detection channel to UV or visible light.

Kits for separating and detecting analytes of a biological sample are also provided in the first aspect of the invention. One such kit includes the device of claim described above and a separation medium. The kit can further include a detection medium. Another such kit includes the device described above and a detection medium.

In a second aspect of the present invention, a device is provided for separating and blotting analytes of a biological sample. The device includes a top layer, a middle layer, and a bottom layer, wherein: each layer comprises a solid substrate and at least one elongated through-slit in the solid substrate; the layers are planar and in contact with each other, such that the middle layer is sandwiched between the top layer and the bottom layer, and the middle layer is configured to slide relative to the top layer and/or the bottom layer. The device also includes a separation channel defined by a through-slit of the middle layer; a pair of access ports configured to supply materials or electrical current to opposite ends of the separation channel; and a membrane disposed in a through-slit of either the top layer or the bottom layer, wherein the membrane can be aligned with the separation channel by sliding the middle layer relative to the top layer or the bottom layer.

In some embodiments of the device, a through-slit of the top layer is aligned with a through-slit of the bottom layer, such that both through-slits can be simultaneously aligned with the separation channel. In some embodiments, the through-slits in the top layer, middle layer, and bottom layer have approximately equal cross-sectional areas. In some embodiments, the through-slit of the top layer, middle layer, or bottom layer comprises angled walls configured to allow air bubbles to escape.

In some embodiments of the device, the access ports are disposed in the top layer or the middle layer. In some embodiments, at least one access port is coupled to a vacuum or pressure source. In some embodiments, at least one access port is aligned with a separation electrode. The separation electrode can be disposed inside the at least one access port. The at least one access port can have a tapered cross section that varies in area in proportion to the distance from the separation channel.

In some embodiments of the device, the membrane is flush with a surface of the top layer or the bottom layer, the surface being in contact with the middle layer. In some embodiments, the membrane spans the full cross-sectional area of the through-slit in which the membrane is disposed. The membrane can be affixed to the top layer or the bottom layer with a fluid-tight seal.

In some embodiments of the device, the middle layer contacts the top layer or the bottom layer through a fluid-tight interface, such that when the separation channel is enclosed by a solid surface of the top layer or the bottom layer, fluid accommodated in the separation channel cannot escape the separation channel through the interface. In some embodiments, a surface of the top layer or bottom layer in contact with the middle layer is coated with a lubricant. The lubricant can be an inert oil. In some embodiments, a surface of the top layer or bottom layer in contact with the middle layer is hydrophobic. In some embodiments, the top layer, the middle layer, or the bottom layer is transparent to UV and/or visible light. In some embodiments, the top layer, the middle layer, and the bottom layer are all transparent to UV and/or visible light.

In some embodiments of the device, the middle layer is wider than each of the top and bottom layers in a dimension parallel to the direction in which the layers are configured to slide. In some embodiments, the middle layer is wider than each of the top and bottom layers in a dimension parallel to the separation channel. In some embodiments, the device further includes a clamp configured to hold the top layer, middle layer, and bottom layer together.

Some embodiments of the device further include a pair of blotting electrodes, wherein: a first blotting electrode is disposed in a through-slit of the top layer; a second blotting electrode is disposed in a through-slit of the bottom layer; and either the first or the second blotting electrode is disposed in the same through-slit as the membrane, on the opposite side of the membrane from the middle layer. In these embodiments, the device can further include a porous support disposed between the membrane and one of the blotting electrodes. Some embodiments of the device further include a porous support disposed in the through-slit of the top layer and/or the through-slit of the bottom layer. Some embodiments of the device further include a detection channel defined by an additional through-slit of the middle layer, wherein the detection channel can be aligned with the membrane by sliding the middle layer relative to the top layer or the bottom layer. An additional access port can be configured to supply materials to the detection channel or remove materials from the detection channel.

In some embodiments of the device, the middle layer comprises a plurality of through-slits defining a plurality of separation channels. In these embodiments: The through-slits of the middle layer can further define a plurality of detection channels. Each separation channel can be adjacent to a detection channel. The middle layer can comprise at least 10, 12, 20, 26, 48, or 96 through-slits. Each of the top layer and the bottom layer can comprise a plurality of through-slits, and at least one through-slit per separation channel.

In the second aspect of the present invention, a system is also provided for automatically separating and blotting analytes of a biological sample. The system includes the device described above, and a motor configured to drive the sliding movement of the middle layer relative to the top layer and/or bottom the layer. In some embodiments of the system, the motor is configured to align the membrane with the separation channel. In some embodiments, the system further includes: a pair of separation electrodes disposed at opposite ends of the separation channel; and a power supply configured to energize the separation electrodes to opposite polarities. In some embodiments, the system further includes: a pair of blotting electrodes, one disposed in a through-slit of the top layer and the other disposed in a through-slit of the bottom layer, wherein one blotting electrode of the pair is disposed in the same through-slit as the membrane, on the opposite side of the membrane from the middle layer; and a power supply configured to energize the blotting electrodes to opposite polarities.

In some embodiments, the system further includes a UV and/or visible light source configured to illuminate the separation channel or membrane. In some embodiments, the system further includes a detector configured to detect light emitted from the separation channel or membrane. In some embodiments, the system further includes a fluid handling subsystem configured to deliver or remove fluid to or from the separation channel, wherein the fluid handling subsystem connects to the access ports.

In the second aspect of the present invention, a method of separating and blotting analytes of a biological sample, using the device described above, is also provided. The method includes: loading the sample in the separation channel; supplying current to opposite ends of the separation channel through the access ports, thereby separating analytes of the sample along the length of the separation channel; sliding the middle layer relative to the top layer or the bottom layer, thereby aligning the membrane with the separation channel; and transferring the analytes from the separation channel to the membrane. In some embodiments of the method, loading the sample in the separation channel comprises introducing a separation medium into the separation channel. In some embodiments, the sample is loaded through at least one of the access ports. In some embodiments, separating the analytes comprises performing electrophoresis, electroosmosis, or isoelectric focusing. In some embodiments, blotting electrodes are disposed in through-slits of the top layer and the bottom layer, and transferring analytes from the separation channel to the membrane comprises energizing the electrodes to opposite polarities. In some embodiments, transferring the analytes comprises filling the through-slit of the top layer and/or the through-slit of the bottom layer with buffer. In these embodiments, transferring the analytes can comprise submerging the device in buffer.

Some embodiments of the method further include detecting the analytes on the membrane. In these embodiments: The device can further comprise a detection channel, and detecting the analytes on the membrane can comprise sliding the middle layer of the device relative to the top layer or the bottom layer, thereby aligning the membrane with the detection channel. A detection reagent can also be flowed through the detection channel. The middle layer can be slid in a first direction relative to the top layer or the bottom layer to align the membrane with the separation channel, and subsequently slid in a second direction relative to the top layer or the bottom layer to align the membrane with the detection channel, the first direction being the opposite of the second direction. Detecting the analytes can comprise disassembling the device and exposing the membrane to detection reagents.

In the second aspect of the present invention, a kit is also provided for automatically separating and blotting analytes of a biological sample. The kit includes the device described above, and a plurality of replacement membranes, wherein the membrane of the device is configured to be replaced with any of the replacement membranes. In some embodiments, the kit further includes a separation medium. In some embodiments, the kit further includes a detection reagent.

BRIEF DESCRIPTION OF THE DRAWINGS

In FIG. 1B, one solid substrate is slid relative to the other, in a direction perpendicular to the long axes of the half-spaces and channels. Thus, a half-space in the top substrate is aligned with different half-spaces in the bottom substrate in FIGS. 1A and C.

FIGS. 5A and C are top views of the device. FIGS. 5B and D are side views of the device. FIGS. 5A and B show the device before sliding the top solid substrate relative to the bottom solid substrate. FIGS. 5C and D show the device after sliding.

FIGS. 7A-C show an embodiment of the two-layer devices described herein, where some of the half-spaces are divided into a plurality of chambers. The chambers are shown in zig-zag patterns in FIG. 7A. FIGS. 7B and C illustrate sliding one solid substrate past the other, thereby translating an α first half-space past a plurality of β second half-spaces. Each of these β half-spaces is divided into a plurality of chambers, which can contain capture agents. Thus, upon sliding, analytes in the α first half-space can be dispensed or fractionated into chambers of some or all of the β second half-spaces, where the analytes can then be immobilized.

DETAILED DESCRIPTION OF THE INVENTION

I. Introduction

Figure 1A:
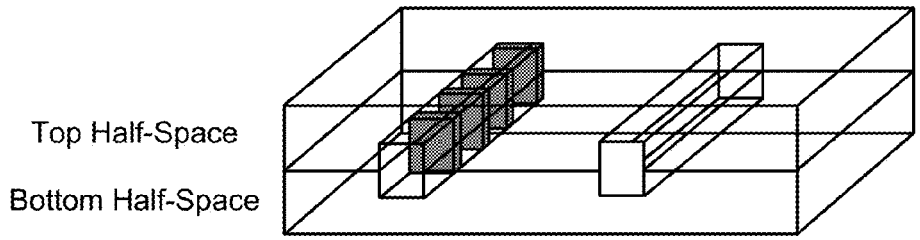
FIGS. 1A-C show a two-layer device according to embodiments of the present invention. The device includes two solid substrates. A surface of each substrate has half-spaces disposed therein and is in contact with the surface of the apposing substrate. The half-spaces of the top and bottom substrates are shown aligned in FIGS. 1A and 1C to form channels.
Figure 1B:
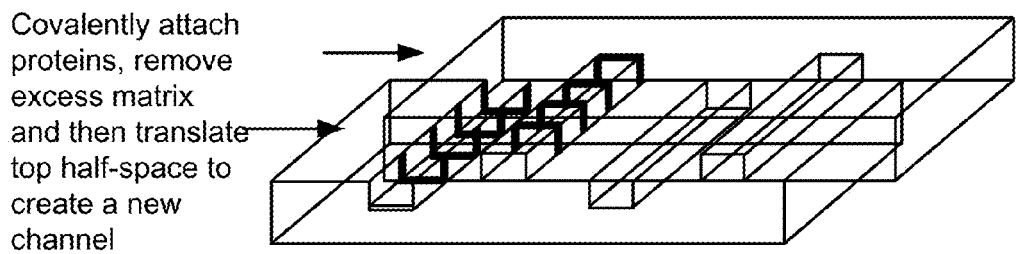
Figure 1C:
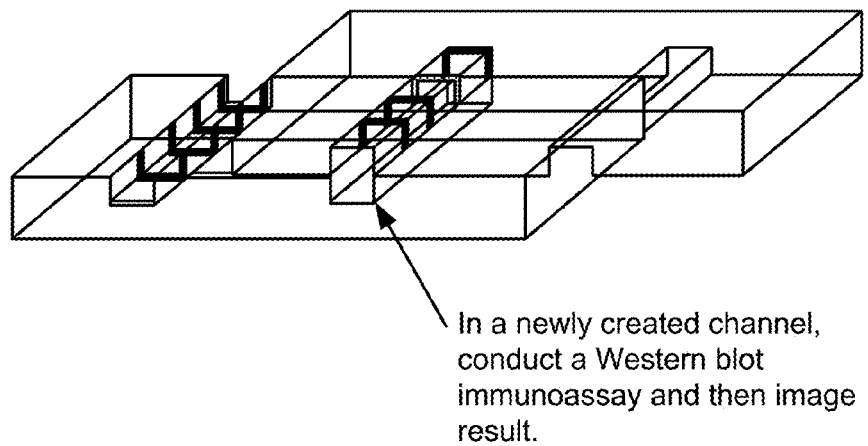
Figure 2A:
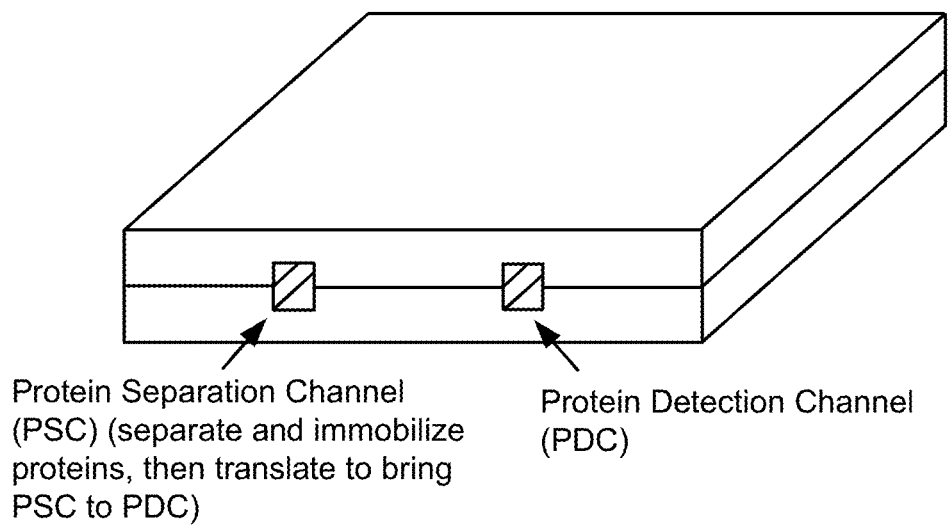
FIGS. 2A-B provide three-dimensional views of a two-layer device according to embodiments of the present invention.
Figure 2B:
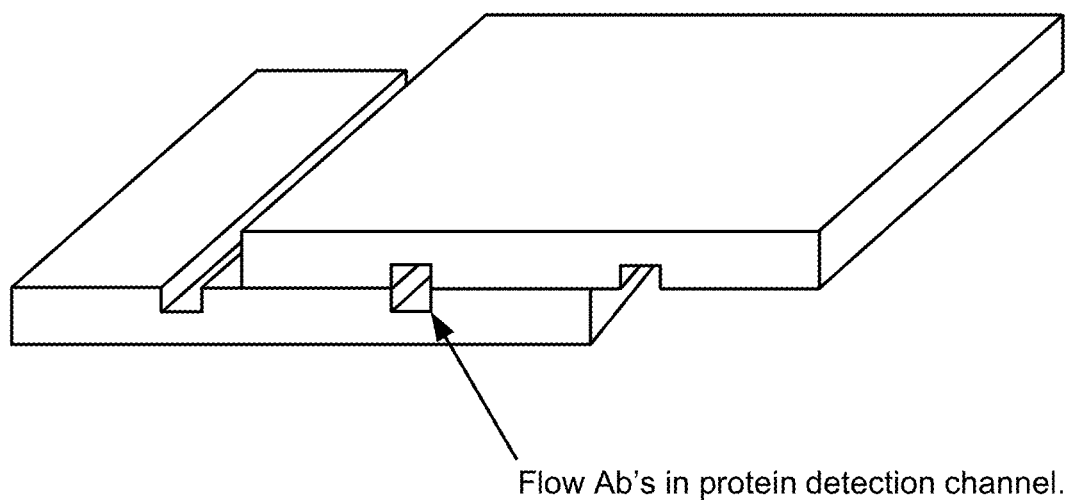

The inventors have found that many of the problems associated with traditional electroblotting can be addressed by separating, immobilizing, and detecting analytes of a biological sample in slideable devices. These devices have two, three, or more solid portions with channels or slits disposed therein. The channels or slits can be exposed on the surfaces of the solid portions, including at the interfaces between the solid portions. Sliding one solid portion of a device relative to other solid portions can change the registration, alignment, orientation, or fluidic contact among the channels or slits, thereby allowing, for example, analytes distributed or immobilized in a channel to be exposed to a new chemical environment. The channels or slits can be of microfluidic dimensions and can be connected to access ports for supplying materials or electrical current. Some embodiments of the devices allow for highly multiplexed sample processing. Provided herein are devices, methods, systems, and kits for separating, immobilizing, blotting, and/or detecting analytes of biological samples.

II. Definitions

"Analyte" refers to a molecule or molecular complex that can be subjected to analysis as provided herein. Analysis can include separation of a molecule from other molecules, followed by immobilization, blotting, and/or detection. Analytes can be biological in origin or can be synthetic. Analytes can include peptides, proteins, nucleic acids, carbohydrates, lipids, viruses, metabolites, hormones, cofactors, vitamins, drugs, and/or small molecules. Without limitation, analytes can be polar, charged, hydrophilic, hydrophobic, monomeric, oligomeric, or polymeric and can have any molecular weight.

"Sample" refers to any biological sample that contains analytes to be separated as discussed herein. The sample can be obtained from any source, such as cells, groups of cells, tissues, or entire organisms, living or dead. The sample can be a cell lysate, tissue homogenate, or sample of blood, saliva, urine, cerebrospinal fluid, or other bodily fluid, among other possibilities. The sample can also be an in vitro preparation of molecular species, for example PCR-amplified DNA or purified proteins.

"Separation medium" refers to a material in which analytes of a sample can be separated from each other, for example by migrating through the material at different rates. The term can refer to the material used to separate analytes of a single sample, or can refer collectively to all the material used to separate analytes of multiple samples.

"Immobilize" and its grammatical equivalents refer to reducing the rate of movement of an object, such as an analyte. Immobilization of an analyte undergoing diffusive or directed motion, for example in an aqueous or gelatinous medium, can be achieved by binding the analyte to another object such as a fixed surface, by freezing the medium, or other known methods.

"Capture agent" refers to a chemical moiety or a material coupled to a surface and by which analytes can be captured. 'Capture' can involve any kind of physical association between the analytes and capture agent, such as specific, non-specific, covalent, or non-covalent binding. Upon capture by a capture agent, analytes are immobilized on the surface.

"Complementary in shape" refers to the shapes of at least two half-spaces, as provided herein, wherein one half-space is disposed in the surface of a first solid substrate, one half-space is disposed in the surface of a second solid substrate, and the surfaces of the first and second solid substrates are in contact with each other. The shapes of the half-spaces are complementary if the half-spaces can be aligned to form a channel (for example, a separation channel or a detection channel), such that the two half-spaces are in fluidic contact along substantially the entire length of the channel. Half-spaces that are complementary in shape can have equal lengths and traverse similarly shaped paths in their respective surfaces (for example, both half-spaces are straight, or both half-spaces are curved).

The terms "about" and "approximately equal" are used herein to modify a numerical value and indicate a defined range around that value. If "X" is the value, "about X" or "approximately equal to X" generally indicates a value from 0.90 X to 1.10 X. Any reference to "about X" indicates at least the values X, 0.90 X, 0.91 X, 0.92 X, 0.93 X, 0.94 X, 0.95 X, 0.96 X, 0.97 X, 0.98 X, 0.99 X, 1.01 X, 1.02 X, 1.03 X, 1.04 X, 1.05 X, 1.06 X, 1.07 X, 1.08 X, 1.09 X, and 1.10 X. Thus, "about X" is intended to disclose, e.g., "0.98 X." When "about" is applied to the beginning of a numerical range, it applies to both ends of the range. Thus, "from about 6 to 8.5" is equivalent to "from about 6 to about 8.5." When "about" is applied to the first value of a set of values, it applies to all values in that set. Thus, "about 7, 9, or 11%" is equivalent to "about 7%, about 9%, or about 11%."

III. General Methods

A. Separation

Separating analytes of the sample can be performed as desired, for example using electrophoresis, electroosmosis, or isoelectric focusing. Descriptions of these techniques can be found in Sambrook and Russell, *Molecular Cloning: A Laboratory Manual* ($3^{rd}$ ed.), New York: Cold Spring Harbor Laboratory Press, 2001 and elsewhere. Any separation medium appropriate for the chosen separation technique can be used, and this medium can have any composition and occupy a channel of any dimensions. When analytes are separated using electrophoresis, for example, the separation medium can be a gel or electrolyte solution. In some embodiments, the separation medium comprises a polymer matrix, hydrogel, or crosslinked polymer. Examples of crosslinked or crosslinkable polymers commonly used in gel electrophoresis are polyacrylamide and polyacrylamide-bisacrylamide. Another example is N,N-polydimethylacrylamide, which may be preferable in capillary gel applications for reducing electroosmotic flow. Examples of polymer matrices include dextran and agarose.

Many variations in the composition of the separation medium are possible. The pore size of polyacrylamide gels can be varied by changing the relative concentrations of acrylamide and bisacrylamide cross-linker. Polyacrylamide gels can also be prepared with gradients of pore sizes, with separate stacking and resolving portions, or with denaturants. In some embodiments, the separation medium includes a denaturant such as sodium dodecyl sulfate (SDS) or urea to ensure that analytes such as proteins or nucleic acids remain denatured during separation. When the analytes are proteins, a reducing agent such dithiothreitol (DTT) or 2-mercaptoethanol can also be included in the separation medium to reduce disulfide bonds. Alternatively, in other embodiments, denaturants and reducing agents can be omitted to ensure that analytes retain their native structures while undergoing separation. The separation medium can have any composition compatible with immobilization or blotting of analytes.

In general, analytes are separated in the separation medium along a separation axis. This axis can correspond to the direction of analyte migration in electrophoresis, the direction of mobile phase flow in column chromatography, or the direction of fluid flow in microfluidic channels.

B. Immobilization

The present devices can in some embodiments immobilize analytes through direct interactions. The devices can be fabricated, using appropriate materials and methods, to retain analytes through adsorption to a surface of a solid substrate or absorption into the body of one of the solid substrates. Alternatively, or in addition, the device can include a capture agent. Under the definition provided above, a capture agent is any chemical moiety or material by which analytes can be captured, such that the analytes become immobilized in the device. The capture agent can be used for specific or non-specific immobilization, can become linked to an analyte covalently or non-covalently, and can act reversibly or irreversibly. The capture agent can be presented on a surface of the device, on beads or other objects decorating a solid substrate, in pores of the solid substrate, or anywhere else accessible to analytes that have been separated in a separation medium. In some embodiments, the capture agent is a crosslinker such as benzophenone, discussed further below. In other embodiments, the capture agent is an affinity structure. The affinity structure can be an antibody, enzyme, protein (e.g., avidin or streptavidin), peptide, aptamer, ligand, nucleic acid, modified nucleic acid, nucleic acid analog, nucleotide, small molecule (e.g., biotin), coordination complex, natural or synthetic polymer, carbohydrate, lectin, nanoparticle, or other binding partner for one or more analytes of interest. In still other embodiments, the capture agent can be a membrane such as nitrocellulose or polyvinylidene fluoride on which analytes can be deposited.

Capture agents can be attached to the device as desired, and multiple capture agents can be included in the same device or solid substrate. In some embodiments, a capture agent is attached to a surface through a linker, such as a polypeptide (e.g., polyglycine or polyalanine), polymer linker (e.g., polyethylene glycol, polyvinylpyrrolidone, polyacrylamide, polydimethylacrylamide, or dextran), dendrimer, unbranched saturated alkyl chains, or the like. Linkers can increase the reach of capture agents in the present devices, and increase the functional surface area of channels in which the capture agents are disposed. For example, a capture agent can be presented on a linker that acts as a molecular scaffold, extending into the interior of a channel, instead of or in addition to on the surface of the channel. Bi- or multi-functional binding agents, such as those disclosed in U.S. Pat. No. 7,935,489, can also be used to extend the reach of capture agents into the interiors of channels. Such binding agents, when dispersed within the separation medium in a channel, can interact simultaneously with capture agents on the channel surface and analytes in the separation medium, thereby increasing the sensitivity of analyte detection.

Immobilization can occur as desired, using any chemistry, catalyst, or stimulus. In some embodiments, immobilizing analytes within a device includes covalently linking the analytes to a surface. Covalent immobilization can be accomplished using a crosslinker, which in this context is any chemical that reacts with moieties on both an analyte and the surface, resulting in the analyte and surface being linked together. Chemical crosslinkers are reviewed, for example, in Johnson and Spence (Eds.), *Molecular Probes Handbook—A Guide to Fluorescent Probes and Labeling Technologies* (11th ed.), Eugene, Oreg.: 2010, and in Hermanson, *Bioconjugate Techniques*, New York: Academic Press, 1996.

In embodiments of the present invention, homobifunctional, heterobifunctional, trifunctional, and zero-length crosslinkers can be used. Homobifunctional crosslinkers each include two identical reactive groups, such as two amines, two thiols (i.e. two sulfhydryls), two acids, or two alcohols. As appropriate, these reactive groups can react with functional groups such as amines, thiols, acids, esters, ketones, and alcohols found in biological analytes and in materials making up the device. Examples of homobifunctional crosslinkers include N-hydroxysuccinimide esters and sulfo-N-hydroxysuccinimide esters, imidoesters, sulfhydryl-reactive crosslinkers (e.g. bis-maleimides), difluorobenzene derivatives, aryl azides, bis-aldehydes (e.g. glutaraldehyde), bis-epoxides, hydrazides, bis-diazonium derivates, and bis-alkylhalides (e.g. iodoacetamides). Heterobifunctional crosslinkers each include two different reactive groups and can react with disparate targets. Examples of heterobifunctional crosslinkers include N-succinimidyl 3-(2-pyridyldithio)-propionate (SPDP) and succinimidyl-4-(N-maleimidomethyl)cyclohexane-1-carboxylate (SMCC) (each reactive with amine and sulfhydryl groups), and 4-(4-N-maleimidophenyl)butyric acid hydrazide (MPBH) (reactive with carbonyl and sulfhydryl groups). Trifunctional crosslinkers, such as 4-azido-2-nitrophenylbiocytin-4-nitrophenyl ester (ABNP) and sulfo-N-hydroxysuccinimidyl-2-(6-[biotinamido]-2-(p-azido benzamido)-hexanoamido) ethyl-1,3'-dithiopropionate (sulfo-SBED), include three reactive groups. Zero-length crosslinkers facilitate or catalyze the formation of covalent bonds between two molecules but are not incorporated into the product of the crosslinking reaction. Examples of zero-length crosslinkers include carbodiimides such as 1-ethyl-3-(3-dimethylaminopropyl)carbodiimide (EDC) and dicyclohexyl carbodiimide (DCC).

In some embodiments, crosslinkers used for immobilization include photoreactive groups. These groups can react with functional groups on nearby analyte molecules upon exposure to light. One such photoreactive group is benzophenone, which can attack a carbon-hydrogen bond in an analyte molecule upon UV illumination. The reaction causes displacement of the hydrogen atom and formation of a new carbon-carbon bond between the analyte and the benzophenone group. Benzophenone is one of many aryl ketones that can be used in crosslinking reactions; other aryl ketones include acetophenone, anthraquinone, anthrone, and derivates thereof. Other classes of useful photoreactive groups include quinones, aryl azides, fluorinated aryl azides, acyl azides, azido formates, sulfonyl azides, phosphoryl azides, diazo alkanes, diazoketones, diazoacetates, diazirines, and ketenes. Some reactive groups within these and related classes react spontaneously with analyte functional groups in the absence of light, and are said to be thermoreactive. These reactive groups can also be useful for crosslinking Photoreactive and thermoreactive groups can be part of bifunctional, trifunctional, or zero-length crosslinkers.

The choice of an appropriate crosslinker for immobilizing a particular analyte on a surface depends on the chemistry of the analyte and materials in the device, among other factors. Crosslinkers for use in embodiments of the invention are not limited to those listed above; any desired variations or combinations of reactive groups can be used. If analytes with disparate chemistries are to be immobilized to the same surface, then multiple crosslinkers can be used. Moieties on the analyte(s) and surface can be reacted with crosslinkers simultaneously or sequentially, with any order or timing. In some embodiments, the surface is pre-treated with a crosslinker, e.g. a bifunctional crosslinker, which becomes linked to the surface before the surface is exposed to analytes. Pre-treatment leaves one reactive group of the crosslinker exposed on the surface, available to react with analytes, and this reaction is effective to capture analytes in the device.

Covalent immobilization can also occur in the absence of crosslinkers. In some embodiments, the device is prepared such that reactive moieties occur directly on a surface, making a crosslinker unnecessary for immobilizing analytes. In these embodiments, the reactive moieties serve as capture agents. Such moieties can include the reactive groups discussed above, for example, succinimides, iodoacetamides, and maleimides, among others. Reactive moieties can be exposed on the surface by removing protecting groups or functionalizing the surface, for example. If desired, these moieties can be separated from the surface by linkers or spacers to increase accessibility for reaction, reduce steric hinderance, and/or reduce non-specific binding. Examples of linkers include polypeptides (e.g. polyglycine or polyalanine), polymer linkers (e.g. polyethylene glycol, polyvinylpyrrolidone, polyacrylamide, polydimethylacrylamide, or dextran), dendrimers, and unbranched saturated alkyl chains. Generally, any chemistries, reaction mechanisms, or linkers, such as those provided in U.S. Pat. Nos. 6,348,596 and 7,935,489, can be used to covalently link analytes to a surface of the device. For example, a functional group on the analyte can serve as a nucleophile and a moiety on the surface can serve as an electrophile, or vice versa. Chemistries for coupling biological analytes to various reactive moieties, materials, and surfaces are well known in the art.

Analytes can also be immobilized within the devices through non-covalent linkages. In some embodiments, one or more affinity structures are disposed within a channel, through-slit, or half-space, for example coupled to the surface of a solid substrate, and can bind non-covalently to analytes in the separation medium, thereby immobilizing these analytes. Examples of such affinity structures include antibodies, enzymes, proteins, peptides, aptamers, nucleic acids, nucleotides, or small molecules. An affinity structure can be any kind of binding partner for an analyte of interest. If the analytes are proteins, for example, an affinity structure can be a ligand or substrate for an analyte, or an antibody that recognizes and binds specifically to an analyte. If the analytes are nucleic acids, an affinity structure can be a DNA- or RNA-binding protein, or another nucleic acid with sequence complementarity for a particular analyte. Binding between an affinity structure and analyte can occur with any degree of affinity or specificity, although higher affinity and specificity can lead to more robust immobilization and detection. Affinity structures can be coupled to a solid substrate as desired, using any appropriate chemistry or surface treatment.

Immobilizing analytes within or adjacent to a separation channel can also include depositing the analytes on a membrane. In some embodiments, particularly when the analytes are proteins, the membrane can include nitrocellulose or polyvinylidene fluoride. As is known in the art, these materials have affinity for proteins but do not react with them, and can bind proteins reversibly while keeping them functionally (e.g., enzymatically) active. If desired, other membrane materials having similar characteristics can be used instead or in addition. The membrane can be attached to a separation channel as desired, for example with adhesive or with fasteners, can coat the channel (or a half-space forming the channel), or can be affixed to one or more individual surfaces of the channel. In some embodiments, the membrane is disposed in a through-slit with which the separation channel is aligned.

The mechanisms available for immobilizing analytes within the present devices are generally unrestricted and can be exploited as convenient and desired. Possible determinants of these mechanisms include the makeup of the sample being studied, the characteristics of analytes of interest (e.g., molecular weight or charge), the composition of the separation medium, and the structure of the separation channel. In some embodiments, analytes are immobilized within a separation channel by adsorption, electrostatic interactions, ionic interactions, or hydrophobic interactions. In some embodiments, immobilizing the analytes can include exposing the separation channel to light, heat, or an altered chemical environment. Light can be used to crosslink analytes to a surface of the device, as discussed above, or to covalently modify analytes or their binding partners for reaction, for example by releasing UV-labile protecting groups. Heat can be used, for example, to denature analytes or contaminants from the sample or to accelerate binding reactions between analytes and moieties in a separation channel. An example of altering the chemical environment of the separation channel is changing the buffer in the channel and thereby exposing analytes to an altered pH. Analytes can be immobilized within the device specifically or non-specifically.

C. Detection

Once immobilized within a half-space of the device and/or on a membrane, analytes of a sample can be detected as desired, using any convenient technique. In some embodiments, analytes of interest can be detected on a half-space if they incorporate detectable labels or are linked or conjugated to such labels. Examples of detectable labels include chromophores, fluorophores, and radioactive isotopes. Analytes can also be detected directly, in the absence of labels, if they are optically active. For example, proteins and nucleic acids absorb infrared and ultraviolet radiation and can also exhibit fluorescence. Accordingly, these analytes can be detected by directing light of an appropriate wavelength on the half-space and measuring an interaction between the light and the analytes. For protein analytes containing tryptophan residues, fluorescence can be enhanced by contacting the analytes with any of several halo-substituted organic compounds, such as chloroform, 2,2,2-trichloroethanol, or 2,2,2-trichloroacetic acid, in the presence of UV radiation. As described in U.S. Pat. Nos. 7,569,130 and 8,007,646 and elsewhere, under such conditions a UV light-induced reaction occurs between the indole moiety of tryptophan and the halo-substituted organic compound, resulting in a fluorescent compound that emits at visible wavelengths.

Detection of immobilized analytes can make use of any labels directly or indirectly linked to the analytes, such as those described in U.S. Pat. Nos. 6,165,800, 6,395,503, 6,972,326, and 7,935,489. In some embodiments, the detected labels are fluorescent. Fluorescent dyes that can serve as labels include fluoresceins, rhodamines, coumarins, BODIPYs, and cyanines Other fluorescent dyes can be used and are reviewed, for example, in Johnson and Spence (Eds.), *Molecular Probes Handbook—A Guide to Fluorescent Probes and Labeling Technologies* (11th ed.), Eugene, Oreg.: 2010. Fluorescent dyes can be conjugated to analytes as desired, using enzymatic addition, Click chemistry, or the Staudinger ligation, among other techniques. In addition to organic dyes, quantum dots ("Q-dots") and fluorescent polymer nanoparticles (polymer dots or "P-dots") can serve as fluorescent labels. Quantum dots having any size, color, or composition can be used, and can be prepared and conjugated to analytes as desired (methods are reviewed, for example, in Medintz et al., *Nature Materials* 4: 435-446, 2005). Similarly, any polymer dots, such as those described in Wu and Chiu, *Angewandte Chemie* 52: 3086-3109, 2013 and elsewhere, can be conjugated to analytes for detection. Fluorescence can also be imparted to analytes by attaching these analytes to fluorescent proteins such as green fluorescent protein (GFP) or yellow fluorescent protein (YFP), which can serve as labels. In recombinant expression systems, a fluorescent protein can be synthesized along with a protein analyte as part of the same polypeptide, such that the fluorescent protein and analyte are covalently tethered together and one renders the other detectable.

In some embodiments, analytes are detected using chemiluminescence. These embodiments involve a chemiluminescent substrate, often a small molecule, that undergoes a chemical reaction and emits light. Some reactions of chemiluminescent substrates can be enzymatically catalyzed. For example, luminol oxidation is catalyzed by peroxidases. The light-emitting decomposition of various phosphorylated 1,2-dioxetanes is catalyzed by phosphatases, and the decomposition of galactose-substituted 1,2-dioxetanes is catalyzed by galactosidase. Tyramide derivatives, as used in tyramide signal amplification techniques, can be converted to tyrosine-reactive free radicals by peroxidases. Any of these systems, or others known in the art, can be used to detect an analyte of interest by coupling the substrate or the enzyme to the analyte. Thus, either the substrate or the enzyme can serve as a detectable label for the analyte. Upon contacting the substrate with the enzyme, light emission is colocalized with the analyte. Chemiluminescent systems from living organisms (i.e., bioluminescent systems) can also be harnessed for analyte detection. For example, luciferin can be coupled to an analyte and detected upon exposure to luciferase or aequorin. Preferably, any coupling of a chemiluminescent substrate, or an enzyme for this substrate, to an analyte for purposes of detection does not interfere with reactions of the substrate. In some embodiments, enzymes used in chemiluminescent detection are coupled to analytes of interest through biotin-avidin linkages. For example, one or more polypeptides of the enzyme can be covalently linked to avidin, and an analyte can be biotinylated. Thus, the enzyme and analyte become linked due to binding between the biotin and avidin moieties.

In other embodiments, detecting the analytes includes contacting the half-space or membrane with a binding partner for one or more analytes of the sample, and detecting a signal indicative of binding between the binding partner and the one or more analytes. This kind of detection can be similar to that used in traditional electroblotting (for example, Southern blotting, northern blotting, and western blotting) and can make use of detection reagents and apparatus used in electroblotting. The binding partner can include an antibody, enzyme, protein, peptide, aptamer, nucleic acid, nucleotide, or small molecule. In particular, when analytes of the sample are proteins, the binding partner can be an antibody. This antibody can be directed to an epitope in one or more analytes of interest. The antibody can be detectable directly, for example by bearing a fluorescent label, or can be detectable using a secondary antibody and/or chemiluminescence. When analytes of interest are nucleic acids, the binding partner(s) can be complementary nucleic acid sequences bearing fluorescent or radioactive labels. Other probes for various types of analytes are known, and many types of signal indicative of binding can be detected. In some embodiments, the signal includes chemiluminescence, electroluminescence, fluorescence, infrared radiation, radioactivity, color, or optical absorbance. In some embodiments, the signal arises from surface plasmon resonance (SPR) and indicates an interaction between the analytes and binding partner occurring on the surface of the half-space. Detection using SPR can employ any appropriate material on the surface of the half-space, for example silver or gold, and can occur in the absence of an optically active moiety or label on the analytes or binding partner. In general, the analytes and binding partner can be part of a biosensor system, which can employ additional molecular components or detection apparatus.

The signal arising from the binding between an analyte and its binding partner can be amplified using any convenient technique. For example, when an analyte is detected using one or more antibodies, the signal can be amplified using tyramide radicals. The signal can also be amplified using a proximity ligation assay, in which two different oligonucleotide-linked antibodies colocalize, so that the oligonucleotides can be ligated together and amplified. Instead or in addition, one or more detectable labels, such as fluorophores, polymer dots, or quantum dots, can be conjugated to the analyte and/or binding partner to supplement signals such as those discussed above. Conjugation can employ biotin-avidin interactions, for example. If a fluorophore is coupled to each of the analyte and binding partner, and the two fluorophores have overlapping excitation and emission spectra, then binding can be detected using fluorescence quenching or fluorescence resonance energy transfer (FRET). In some embodiments, additives such as crowding agents (e.g., polyethylene glycol or dextrans) are contacted with a surface during detection to increase the rates of binding between an analyte and its binding partner.

If desired, two or more binding partners can be used, simultaneously or at different times, to detect analytes on the same surface. The binding partners can be specific for the same analyte, different forms (e.g., phosphorylated and unphosphorylated) of the same analyte, or different analytes entirely. These binding partners can give rise to the same signal, measurably different signals (for example, fluorescence of different emission wavelengths), or orthogonal types of signals (for example, fluorescence and radioactivity). Using multiple binding partners can provide more informative analyte detection than is possible with a single binding partner. For example, two binding partners can reveal the relative amounts of two different analytes immobilized in the device or the relative positions of the analytes in the device. Alternatively, two different antibodies directed to the same analyte can probe for the presence, integrity, or accessibility of two different epitopes.

Detecting analytes immobilized on a half-space or membrane can require, in some embodiments, exposing the binding partner for the analytes to a reagent. The reagent can bind to or react with the binding partner in order to generate a detectable signal. For example, if the analytes are proteins and the binding partner is an antibody, the reagent can be a chemiluminescent substrate (e.g., luminol) that can be oxidized by a horseradish peroxidase domain coupled to the antibody. The substrate can be added to a solution in contact with the half-space or membrane having the immobilized analytes, and in some embodiments, does not become coupled to the analytes or antibody, but the chemiluminescent signal reveals the location of antibody-bound analytes. In order to amplify the light emitted by oxidation of the substrate and achieve enhanced chemiluminescence, a chemical such as p-iodophenol can also be added. When an antibody serves as binding partner to the analytes, the reagent used for purposes of detection can alternatively be a labeled secondary antibody. Detection can make use of multiple reagents in addition to the binding partner.

In some cases, detecting analytes can involve applying a blocking agent to the half-space or membrane on which the analytes are immobilized. The blocking agent can bind non-specifically, for example in locations where analytes are not immobilized, and prevent binding partners for the analytes from also binding non-specifically in these locations. The blocking agent can thus reduce background signal and allow more precise detection of analytes. Examples of blocking agents include proteins such as bovine serum albumin or milk proteins. Preferably, the blocking agent is applied to the half-space or membrane before the half-space or membrane is contacted with binding partners.

Any apparatus can be used to detect analytes immobilized in the present devices, directly or with the aid of a binding partner or reagent. For example, a film or digital camera, coupled if necessary to an appropriate illumination source, can be used to detect color, fluorescence, chemiluminescence, and other types of optical signals arising from analytes on a half-space or membrane. Images can be stored and processed as desired, for example to quantitate the amount of analyte present. Radioactive signals can be detected using a Geiger counter, scintillation counter, or film sensitive to isotopic decay. Other kinds of apparatus can be used in detection.

IV. Two-Layer Devices

Provided herein are devices, methods, systems, and kits for separating analytes of a biological sample. In some embodiments, the devices are constructed from two solid substrates with surfaces in contact. The devices include a plurality of channels (for example, microfluidic channels) formed from indentations in these surfaces. The indentations, also called "half-spaces," can be aligned with each other across the interface between the substrates. Shifting or sliding one substrate relative to the other can change the alignment of the half-spaces and form new channels.

In some embodiments, the method includes the steps of: applying a sample to a separation medium, wherein the separation medium is contained in a microfluidic channel formed by two half-spaces of opposing substrates; separating analytes of the sample in the separation medium along a separation axis; immobilizing the analytes within one or both of the half-spaces; optionally removing the separation medium; sliding one solid substrate past the other along the interface, thereby aligning each half-space comprising the immobilized analytes with a new complementary half-space and forming a new channel; and detecting the analytes immobilized on the half-space in the new channel.

A. Device Structure

Devices according to embodiments of the present invention include solid substrates. A solid substrate can be made of any desired materials, such as plastic, metal, glass, or ceramic. In some embodiments, solid substrates are shaped to be planar, with one or more flat surfaces. The solid substrates can be prepared to be, in whole or in part, impervious to liquids or inert to chemical environments associated with biological samples. These chemical environments can include acidic or basic pH, high salt concentration, or denaturants such as urea, sodium dodecyl sulfate, or beta-mercaptoethanol, for example. In some embodiments, the solid substrates are mechanically rigid and resist deformation from tensile or compressive forces.

The solid substrates can include half-spaces disposed therein. The half-spaces are configured to accommodate fluids or other materials, such as separation media, used for separating and detecting analytes of biological samples. A half-space can be an indentation in a surface of a solid substrate, such as a trench, groove, or trough. Half-spaces can have any desired geometry. For example, they can be linear or curved, and can have square, rectangular, elliptical, or semi-circular cross-sections. In some embodiments, half-spaces have lengths (measured along the surface of the solid substrate) of at least 1, 2, 5, 10, 20, or 50 cm. In some embodiments, half-spaces have widths of at least 0.01, 0.02, 0.05, 0.1, 0.2, 0.5, 1, 2, 5, or 10 mm. In some embodiments, half-spaces have depths of at least 0, 0.01, 0.02, 0.05, 0.1, 0.2, 0.5, 1, 2, 5, or 10 mm. In some embodiments, a half-space has zero depth or a depth of about zero, meaning that the half-space has no discernable depth with respect to the adjacent surface of the solid substrate in which it is disposed. Half-spaces can have microfluidic dimensions. In some embodiments, the half-spaces have sub-millimeter (at most about 1 mm) or low-millimeter (at most about 10 mm) widths and depths to maintain capillary forces in channels formed from the half-spaces. Small channel dimensions can also prevent contact between aqueous solutions in these channels and hydrophobic portions of the device.

Some embodiments of the present devices include two solid substrates that are held in close proximity (FIGS. 1A-C, 2A-B). Surfaces of the solid substrates can contact each other at an interface, and half-spaces can be disposed in these surfaces. Thus, depending on the relative positions of the two solid substrates, two or more half-spaces can be in contact with each other or in fluidic communication across the interface. In some embodiments, the half-spaces on a first solid substrate (i.e., first half-spaces) are complementary in shape to the half-spaces on the apposing second solid substrate (i.e., second half-spaces), so that the first half-spaces and second half-spaces can form channels when appropriately aligned. For example, a first half-space and second half-space, each with a semi-circular cross-section, can form a channel with a circular cross-section when the surfaces containing these half-spaces are in contact and the two half-spaces are aligned along their lengths. It will be recognized that a half-space does not necessarily provide half (i.e., 50%) of the volume of a channel, and the word "half" is used for convenience herein.

In some embodiments, half-spaces are disposed in the surface of a solid substrate in a repeating array (FIGS. 3A-E, 4). For example, there can be two kinds of half-spaces, $\alpha$ and $\beta$, that are arrayed in the surface such that each $\alpha$ half-space is adjacent to a $\beta$ half-space. Thus, one alternately encounters half-spaces of the $\alpha$ and $\beta$ kinds when traversing the surface of the solid substrate. In these embodiments, the half-spaces can be linear and/or parallel to each other, and can have any desired spacing or pitch between the $\alpha$ and $\beta$ half-spaces. For example, the distance between an $\alpha$ half-space and the adjacent $\beta$ half-space can be equal, greater than, or less than distance between the $\beta$ half-space and the next $\alpha$ half-space in the array. A solid substrate can include any desired number of half-spaces, for example at least about 6, 12, 24, 48, 96, 128, 256, or 384 half-spaces or pairs of $\alpha$ and $\beta$ half-spaces.

Half-spaces can include capture agents, as described above, disposed within them. For example, a capture agent can be chemically linked to the surface of the solid substrate within a half-space, or coated on this surface. In some embodiments, $\alpha$ and $\beta$ half-spaces differ in whether they include capture agents, or include different kinds of capture agents or surface treatments. For example, in some embodiments, $\alpha$ half-spaces include capture agents while $\beta$ half-spaces do not. In some embodiments, a first capture agent is disposed on the surface of a first solid substrate, within $\alpha$ half-spaces in this surface (i.e., $\alpha$ first half-spaces), while a second a second capture agent is disposed on the surface of a second solid substrate, within $\alpha$ half-spaces in this surface (i.e., $\alpha$ second half-spaces). The first capture agent and the second capture agent can be the same or different. In some embodiments, the first capture agent or second capture agent is a crosslinker, such as benzophenone, formaldehyde, glutaraldehyde, or any of the other crosslinkers described above. The first capture agent or second capture agent can instead be an affinity structure, such as a protein or nucleic acid. In some embodiments, the first capture agent or the second capture agent is attached to the surface of the respective solid substrate through a linker, such as a polypeptide (e.g. polyglycine or polyalanine), polymer linker (e.g. polyethylene glycol, polyvinylpyrrolidone, polyacrylamide, polydimethylacrylamide, or dextran), dendrimer, or unbranched saturated alkyl chain. Capture agents can be linked to the half-spaces as desired, for example covalently or non-covalently. Capture agents can interact with (e.g., bind to or react with) analytes of biological samples specifically or non-specifically, and reversibly or irreversibly.

Figure 4:
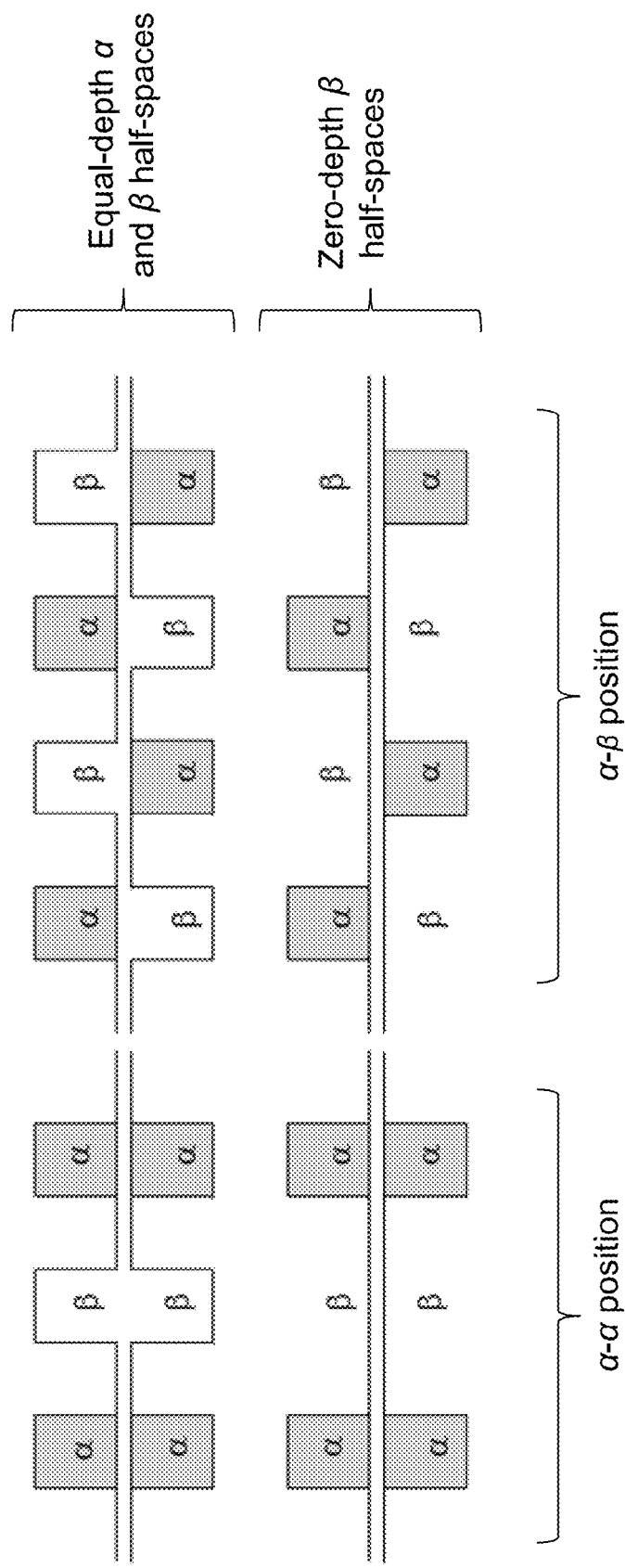
FIG. 4 illustrates α and β half-spaces in embodiments of two-layer devices. The figure is divided into four panels, each showing the two solid substrates of a two-layer device stacked one on top of the other and meeting at a horizontal interface. The half-spaces at the top of each panel, in the first solid substrate, are first half-spaces (i.e., α first half-spaces and β first half-spaces). The half-spaces at the bottom of each panel, in the second solid substrate, are second half-spaces (i.e., α second half-spaces and β second half-spaces). Sliding the first solid substrate past the second solid substrate along the interface realigns the half-spaces from the α-α position (left two panels) to the α-β position (right two panels). In some embodiments (bottom two panels), the β half-spaces have zero depth.
Figure 5A:
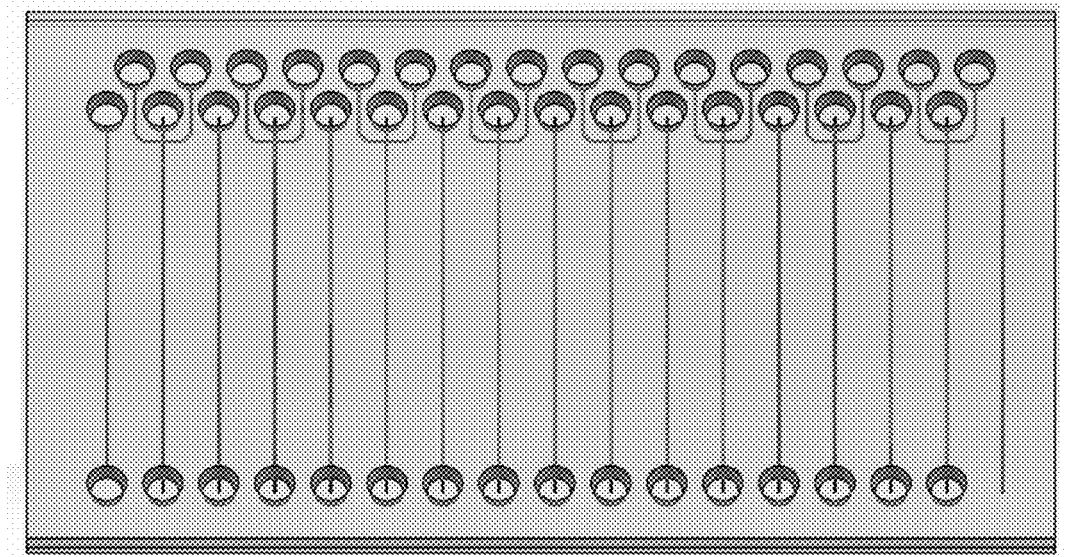
FIGS. 5A-D show an embodiment of a two-layer device. The device has access ports for all half-spaces (e.g., α half-spaces and β half-spaces) in the top solid substrate of the device. The access ports are through-holes in the top solid substrate. At least two access ports are associated with each half-space in the top solid substrate, with at least one access port disposed at either end of each half-space (i.e., at opposite ends). For every other half-space in the solid substrate (e.g., α half-spaces), a plurality of access ports are disposed at one end of the half-space. Two of these access ports are connected by secondary channel segments and form a loading cross.
Figure 5B:
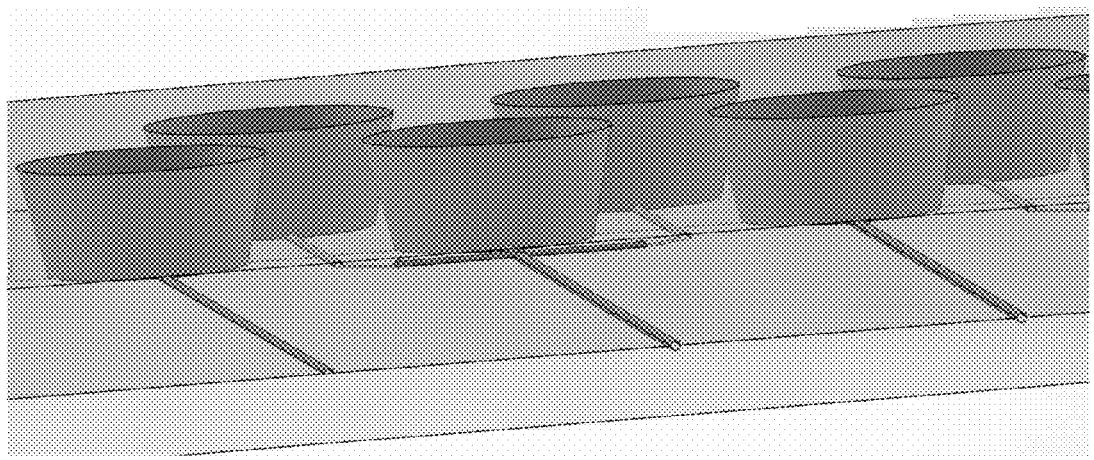
Figure 5C:
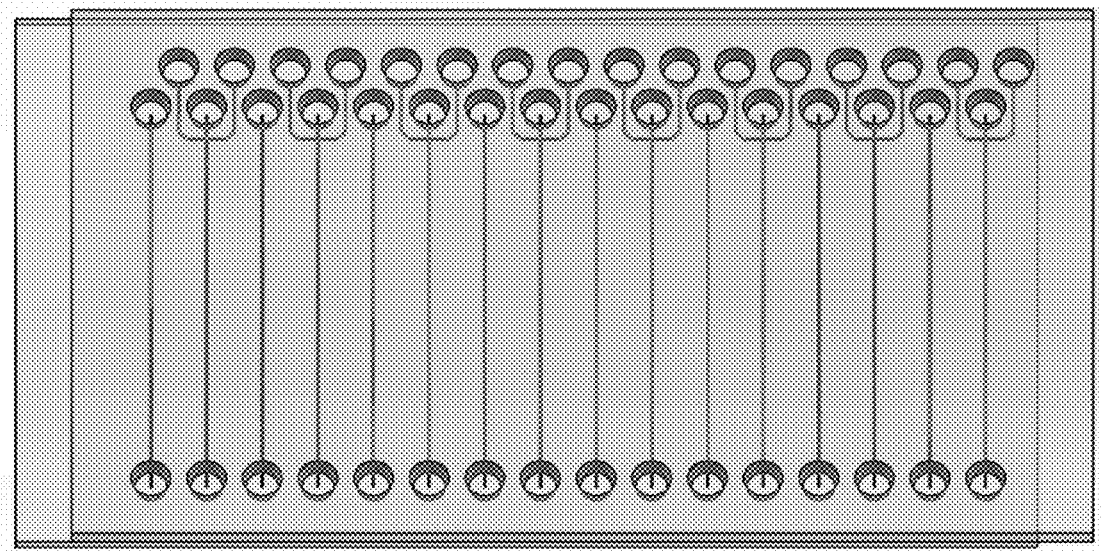
Figure 5D:
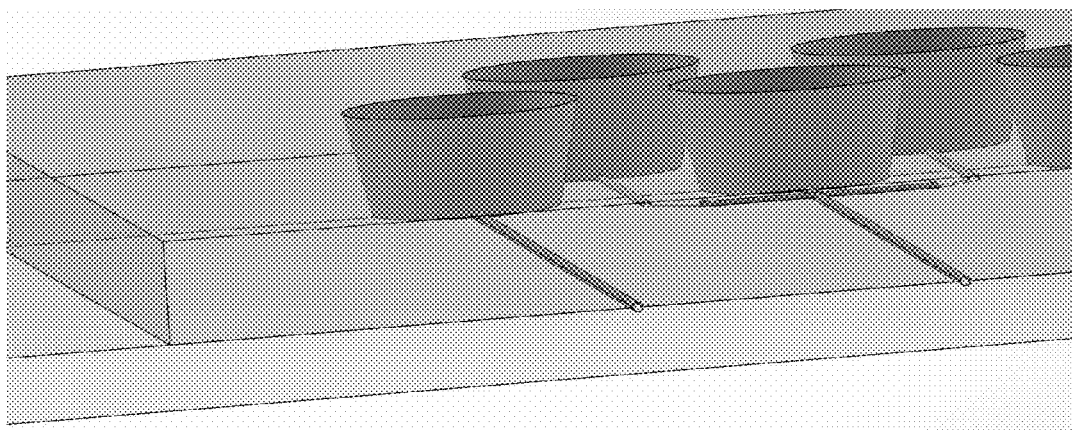
Figure 6A:
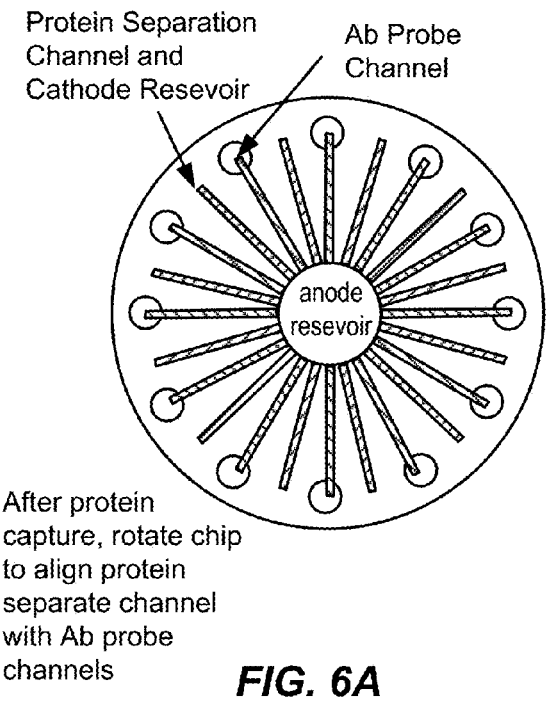
FIGS. 6A-F illustrate an embodiment of the two layer devices described herein. The solid substrates of the device are circular in shape, and half-spaces and channels are oriented radially, extending from the center of the circle to its periphery.
Figure 6B:
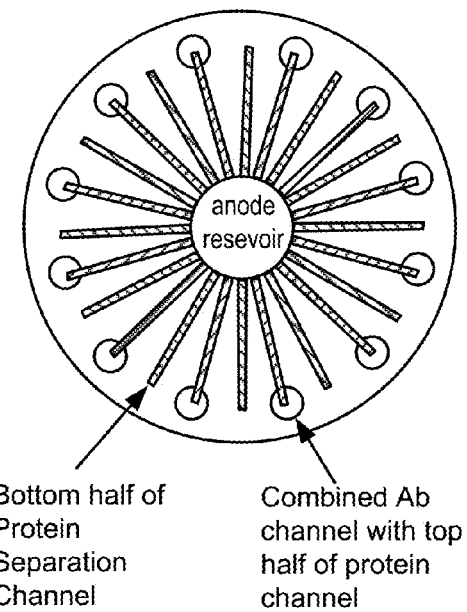
Figure 6C:
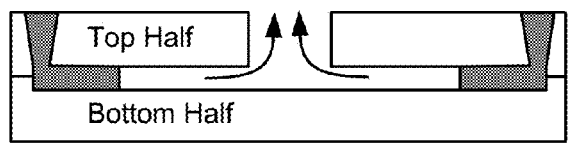
Figure 6D:
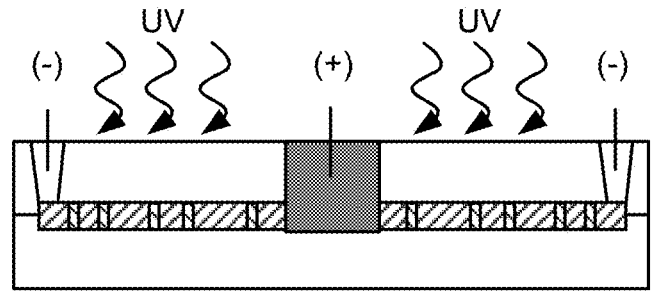
Figure 6E:
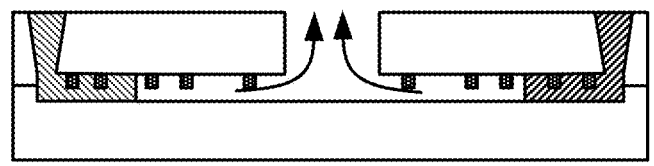
Figure 6F:
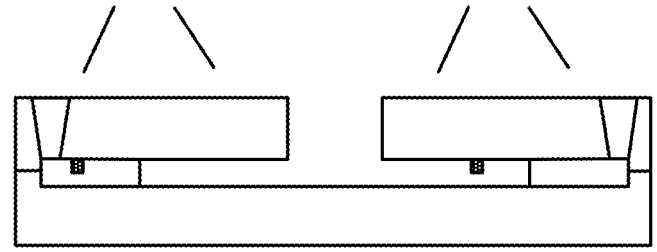

In the two-layer devices described herein, the two solid substrates are configured to slide past each other along their interface. Sliding can change the alignment or registration of any half-spaces disposed in the substrate surfaces when these surfaces are in contact at the interface. For example, in some embodiments, a first solid substrate is configured to occupy two positions relative to a second solid substrate, where the alignment of α and β half-spaces across the interface differs in the two positions (FIG. 4). One position is an "α-α" position, where α half-spaces in the first solid substrate (α first half-spaces) are aligned with α half-spaces in the second solid substrate (α second half-spaces). When so aligned, the α half-spaces in the two solid substrates form separation channels. In this position, β first half-spaces may also align with β second half-spaces. Upon sliding, the first solid substrate can then occupy an "α-β" position relative to the second solid substrate. In this position, the α first half-spaces are aligned with β second half-spaces to form α-β channels, and the β first half-spaces are aligned with α second half-spaces to form β-α channels. The α-β and β-α channels can serve as detection channels.

In some embodiments of the present devices, some or all of the β half-spaces are engineered to be less deep than the α half-spaces in order to prepare detection channels that are shallower than the separation channels. Shallower detection channels can in some cases retain smaller amounts of non-specifically bound analytes after sliding, and thus promote lower background levels for detection. The depths of the β half-spaces in either the first solid substrate or the second solid substrate, or both solid substrates, can be adjusted relative to the counterpart α half-spaces. For example, in some embodiments, one or more β first half-spaces are less deep than one or more α first half-spaces. The depth of at least one β first half-space can be less than the depth of at least one α first half-space, or the depth of every β first half-space can be less than the depth of every α first half-space. Alternatively or in addition, in some embodiments one or more β second half-spaces are less deep than one or more α second half-spaces. The depth of at least one β second half-space can be less than the depth of at least one α second half-space, or the depth of every β second half-space can be less than the depth of every α second half-space.

One half-space can have any desired depth relative to another half-space, regardless of whether the two half-spaces are in the same solid-substrate or apposing solid substrates. For example, a β first half-space can be at most about 5, 2, 1, 0.9, 0.5, 0.2, or 0.1 times as deep as an α first half-space. In some embodiments, at least one β first half-space, at least one β second half-space, or the β first half-spaces and the β second half-spaces of a device have depths of about zero (FIG. 4). In these embodiments, a detection channel comprising a zero-depth β half-space includes an α half-space adjoining the flat surface of the apposing solid substrate. Fluids can flow through the portion of such a channel formed by the α half-space, and access ports (discussed below) leading to the α half-space or the zero-depth β half-space can supply fluids to the detection channel.

In some embodiments, the α first half-spaces are about equal in depth to the β first half-spaces, with the result that half-spaces in the first solid substrate contribute the same amount of depth to every separation channel and detection channel. Instead or in addition, the α first half-spaces can be about equal in depth to the α second half-spaces. In these embodiments, the two α half-spaces forming each separation channel can be symmetrical, and all α half-spaces contribute the same amount of depth to the detection channels. In still other embodiments, the depths of half-spaces in the first solid substrate are uniformly greater than the depths of half-spaces in the second solid substrate. For example, the first half-spaces can have a first depth, the second half-spaces can have a second depth, and the second depth can be less than the first depth. Alternatively, all the half-spaces can have the same depth. For example, the α first half-spaces, the β first half-spaces, the α second half-spaces, and the β second half-spaces can all be about equal in depth.

Sliding between the solid substrates can be facilitated by any desired mechanism. For example, the substrates can be lubricated at the interface or contain tracks, rails, or wheels to constrain the direction of sliding. In some embodiments, the substrates are held together by suction, magnetism, or other attractive forces that can be adjusted or temporarily relieved to facilitate sliding. Alternatively, the substrates can be held together by a clamp or other external apparatus. In some embodiments, such as when the α and β half-spaces in the surface of a solid substrate are parallel to each other, the direction of sliding is orthogonal to the lengths of the half-spaces. For example, each first half-space can be disposed along a separation axis, and the first solid substrate and second solid substrate can be configured to slide past each other such that the first solid substrate or the second solid substrate moves in a direction orthogonal to the separation axis. Alternatively or in addition, the first surface and the second surface (i.e., the surfaces of the first solid substrate and second solid substrate) can be configured to contact each other with a fluid-tight seal. In these embodiments, a fluid contained in an α first half-space, a β first half-space, an α second half-space, a β second half-space, a separation channel, or a detection channel cannot escape from the half-space or channel through the interface between the first and second surfaces.

Figure 3A:
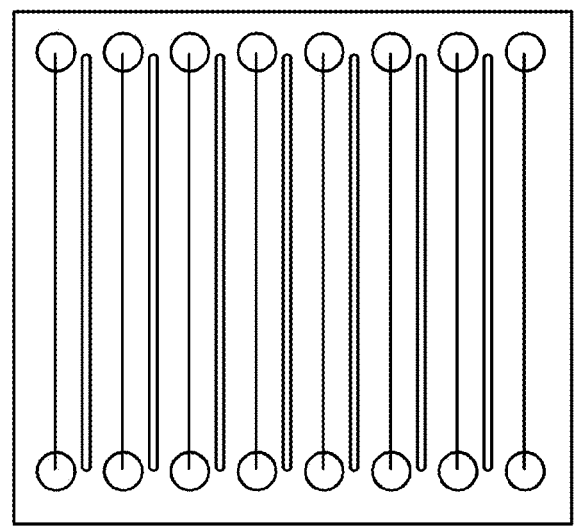
FIGS. 3A-E illustrate a two-layer device and methods of using the device, according to embodiments of the present invention. For every other half-space in the top solid substrate, two access ports are disposed at opposite ends of the half-space. The access ports are through-holes in the top solid substrate, and are used to fill channels formed from the half-space (FIG. 3C) or accommodate electrodes (FIG. 3D). Analytes are immobilized in separation channels formed from half-spaces of the device by UV-induced crosslinking (FIG. 3D).
Figure 3B:
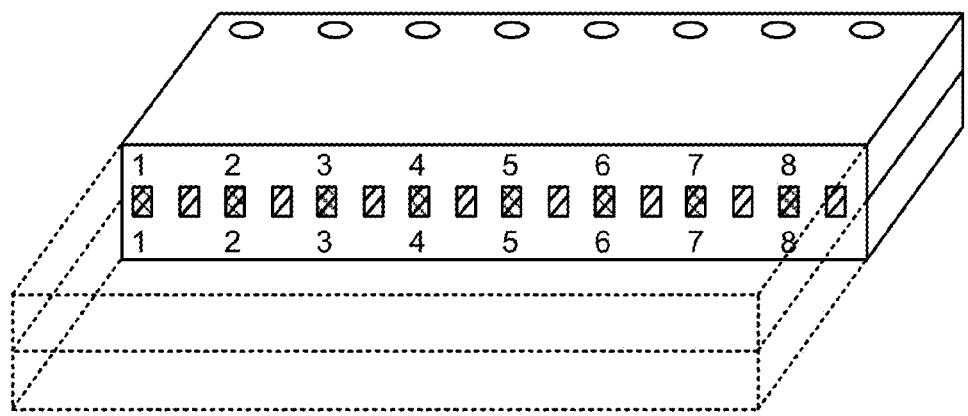
Figure 3C:
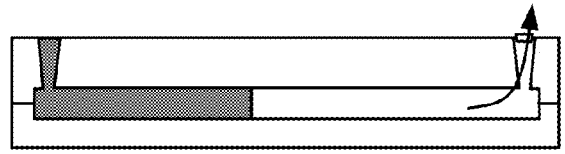
Figure 3D:
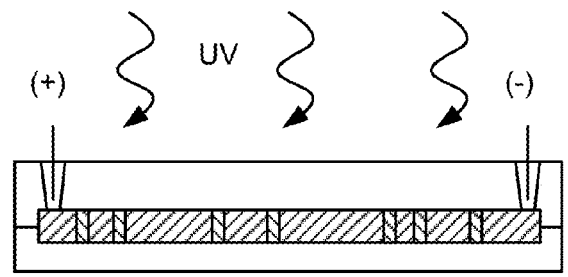
Figure 3E:
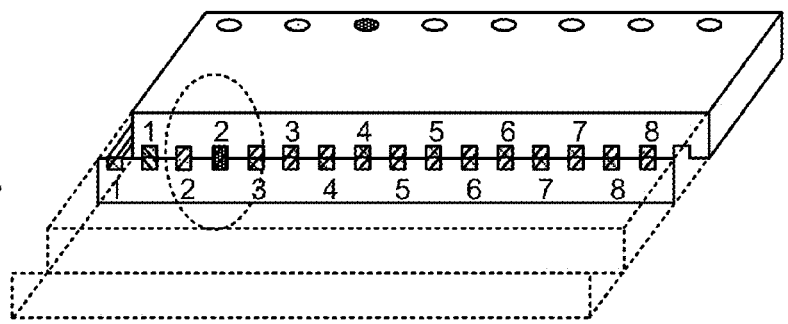

The present devices also include a plurality of access ports, which are configured to provide access to the separation channels and the detection channels resulting from alignment of the half-spaces in the solid substrates. The access ports provide access to these channels from space outside the device. For example, the access ports can be configured to introduce or remove fluids to or from the channels (FIG. 3C). In some embodiments, an access port is coupled to a vacuum source or pressure source. Alternatively or in addition, an access port can be configured to supply electrical current to a channel (such as a separation channel), and can accommodate or be aligned with an electrode (FIG. 3D). As desired, an access port can address one or more separation channels, detection channels, or both separation or detection channels. Similarly, an access port can provide access to either an α half-space or a β half-space, in the first or second solid substrate.

In some embodiments, the access ports comprise through-holes in the first solid substrate and/or the second solid substrate (FIGS. 3C-D, FIG. 5A-D). Through-holes can generally be incorporated into the solid substrates as desired and can have any desired shapes, dimensions, or positions. For example, a through-hole can have a square, rectangular, round, or circular cross-section, and can be straight, tapered, or beveled. In some embodiments, a through-hole has a cross-sectional area of at least 0.1, 0.2, 0.5, 1, 2, 5, or 10 mm$^2$, and a depth of at least 0.1, 0.2, 0.5, 1, 2, 5, or 10 mm. In some embodiments, a through-hole is located at one end of a half-space and can be used to supply fluid to a channel formed from that half-space from the one end. Some embodiments also include two through-holes associated with a half-space or channel, for example at opposite ends of the channel. The two through-holes can be used to simultaneously introduce fluid at a first end of the channel and remove fluid from a second end, thereby causing fluid to flow from the first end to the second end. Alternatively or in addition, the two through-holes can accommodate electrodes of opposite polarities, which can be used to drive current through the channel.

Access ports such as through-holes can be distributed between the first solid substrate and second solid substrate as desired, and similarly can be associated with α half-spaces, β half-spaces, or both. In some embodiments, the access ports comprise through-holes in the first solid substrate, and at least one through-hole provides a passage between each α first half-space and space outside the first solid substrate. One or more of these through-holes can be coupled to a vacuum source or a pressure source, or accommodate an electrode. In some embodiments, two through-holes provide passages between each α first half-space and space outside the first solid substrate, and occur at opposite ends of the α first half-space. The two through-holes associated with an α first half-space can be used as described above to supply materials or current to a separation channel or detection channel formed from the α first half-space. For example, an electrode can be disposed in each of the two through-holes. In some embodiments, in addition to having at least one through-hole per α first half-space, at least one though-hole provides a passage between each β first half-space and space outside the first solid substrate. Thus, through-holes can provide access to all α first half-spaces and β first half-spaces, and all half-spaces in the first solid substrate can be connected to the exterior space (FIGS. 5A-D). As for the α first half-spaces, each β first half-space can be connected to two or more through-holes, which can occur at opposite ends of the β first half-space and be used to supply materials or electrical current to channels formed from the β first half-space. In these embodiments, the through-holes provide access to the separation channels formed from the α first half-spaces when the device is in the α-α position, and provide access to both α-β and β-α detection channels when the device is in the α-β position.

In some embodiments of the device, access ports include through-holes in the second solid substrate as well as the first solid substrate. In these embodiments, at least one through-hole is associated with each α first half-space, and at least one through-hole is associated with each α second half-space. These through-holes provide passages between the α half-spaces and the space outside the respective solid substrates. When the device is in the α-α position, separation channels formed from pairs of α first half-spaces and α second half-spaces can be serviced using the through-holes in either solid substrate. For example, electrodes can be inserted from opposite sides of the device, with one electrode in each solid substrate, to provide current along the length of a separation channel. These embodiments thus provide flexibility for addressing the separation channels. When the device is shifted to the α-β position, each α half-space can become part of a detection channel. Through-holes associated with a half-spaces in the first and second solid substrates can be used to service both α-β and β-α detection channels, for example to introduce detection reagents.

Some embodiments of the device include a plurality of access ports, for example through-holes, associated with each α first half-space, and these access ports can have distinct purposes for facilitating the separation or detection of analytes. For example, at least one access port can be coupled to a vacuum source or a pressure source, and at least one other access port can have an electrode disposed therein. Some or all of the plurality of access ports can occur at the same end of the α first half-space and be used to service channels formed from this half-space. In some embodiments, two access ports are used to supply materials to each α first half-space and are connected to each other through one or more secondary channel segments (FIGS. 5A-D). The secondary channel segments provide a pathway between the two access ports, and this pathway can intersect the α first half-space or run coextensively with the α first half-space along part of its length. Thus, materials passed from one access port to the other through the secondary channel segments can cross or travel along part of the α first half-space, or a channel formed from this half-space, and be positioned to travel along the full length of the channel upon application of a current or other driving force. The two access ports and the secondary channel segments connecting them can thus be used to load the channel, and their intersection with the channel is known in the art as a loading cross.

After analytes of a biological sample have been separated in a separation channel of one of the present devices, the analytes can be immobilized within the separation channel (FIG. 3D). The first solid substrate can then be slid past the second solid substrate, for example from the α-α position to the α-β position, and immobilized analytes can be detected in the resulting detection channels (FIGS. 1B, 1C, 2B, 3E).

In various embodiments of the devices, light is used to immobilize or detect analytes. For example, UV light can be used to crosslink analytes to the half-spaces forming a separation channel, using the capture agents disposed in the channel, and UV or visible light can be used to excite fluorescent analytes or binding partners for detection. Accordingly, in some embodiments, the first solid substrate or the second solid substrate is transparent, in whole or in part, to UV and/or visible light. For example, the solid substrate can be made of a glass or plastic that passes desired wavelengths of light. Examples of transparent glasses are borosilicate glass and fused quartz. Examples of transparent plastics are cyclic olefin polymers and cyclic olefin copolymers. In some embodiments, a device further includes a UV and/or visible light source configured to direct light into the separation channels or detection channels. The light source can be an incandescent bulb, fluorescent bulb, laser, or light-emitting diode, for example, and can be coupled to the first and/or second solid substrate as desired. A device can also include a detector configured to detect light emitted from the detection channels, for example from a fluorescent analyte. Suitable detectors include or make use of photographic film, charge-coupled devices, or complementary metal-oxide-semiconductor devices. Detection strategies are discussed further above.

In addition to embodiments employing parallel half-spaces and channels, embodiments of the present devices can also include half-spaces and channels that are arranged radially. For example, one or both of the solid substrates can be circular in shape, as shown in FIGS. 6A-F, with access ports arranged at the periphery of the circle. In some embodiments, the first half-spaces radiate from and terminate at a central location in the first solid substrate, which occurs roughly at the center of the circle. The first solid substrate is configured to be rotated about the central location, thereby allowing the first solid substrate to slide past the second solid substrate, and allowing half-spaces in the first solid substrate to align with half-spaces in the second solid substrate. The two solid substrates can have α and β first and second half-spaces, and the rotation can alternatively align the solid substrates in α-α and α-β positions as discussed above. In some embodiments, the central location of the first solid substrate serves as an access port in which an electrode can be disposed. Alternatively or in addition, a vacuum source or a pressure source can be coupled to the central location. The central location can serve as an access port for multiple (or all) half-spaces or channels of the device.

Alternate embodiments of the devices, including those with linear and parallel half-spaces, have at least one β half-space divided into a plurality of chambers (FIGS. 7A-C). In some embodiments, these chambers are fluidically segregated from each other. Thus, if the solid substrates are shifted after analyte separation from the α-α to the α-β position, any separation medium present in an α half-space can be dispensed into one of the chambers of a β half-space when the α and β half-spaces align. A β half-space can be engineered to have any desired number of chambers, for example at least about 2, 5, 10, 20, 50, 100, 200, 500, or 1000 chambers. In some embodiments, a β half-space has a density of chambers of at least 1, 2, 5, 10, 20, 50, 100, 200, 500, 1,000, 2,000, 5,000, or 10,000 chambers per $cm^2$, or a density of at least 1, 2, 5, 10, 20, 50, 100, 200, 500, 1,000, 2,000, 5,000, or 10,000 chambers per cm as measured along the long axis of the half-space. The chambers can be arranged in the β half-space as desired, for example in a square or rectangular grid or in a zig-zag pattern. The chambers can have volumes of, for example, at least about 1, 2, 5, 10, 20, 50, 100, 200, 500, 1,000, 2,000, 5,000, or 10,000 picoliters. In some embodiments, a β half-space has multiple chambers disposed at the same location along its long axis. In these embodiments, multiple portions of a separation medium, originating from the same location along the separation axis of a separation channel and possibly containing the same analyte(s), can be dispensed into multiple chambers of a divided β half-space upon shifting the solid substrates. The chambers of a divided β half-space can contain a capture agent, so that immobilization of analytes in the chambers can occur after shifting. Different chambers can contain different capture agents.

B. Methods

The two-layer slideable devices described above can be used to separate and detect analytes of a biological sample. The present methods involve placing the two solid substrates of a device in proximity, such that surfaces of the substrates (a first surface and a second surface) are in contact at an interface and half-spaces disposed in the surfaces are aligned across the interface. While the first solid substrate is in the α-α position relative to the second solid substrate, such that an α first half-space is aligned with an α second half-space to form a separation channel, analytes of a sample are separated in a separation medium contained in the separation channel. The analytes are then immobilized in the separation channel using the first and second capture agents disposed on the surfaces of the solid substrate within the α half-spaces. Subsequently, the first solid substrate is slid past the second solid substrate, from the α-α position to the α-β position, thereby disrupting the separation channel and forming two detection channels. The immobilized analytes can be detected in one or both of the detection channels.

Analytes of a sample can be separated in the device as desired, using electrophoresis, electroosmosis, or isoelectric focusing, as described above. In some embodiments, separation is achieved by inserting one or more electrodes into access ports servicing the separation channel, and appropriately energizing the electrodes. For example, two electrodes can be placed at opposite ends of the separation channel, and energized to opposite polarities, thereby establishing a current flow through the separation channel for electrophoresis.

Some embodiments of the methods include introducing the separation medium into the separation channel prior to the separation step. When the separation medium is flowable, for example in the form of an aqueous polymer solution, the separation medium can be introduced directly through the access ports. If desired, the biological sample can be suspended in the separation medium and flowed into the separation channel along with the separation medium. Alternatively, the separation medium can be allowed to gel or solidify in the separation channel, and the biological sample can then be loaded onto the separation medium through one or more access ports. Solid or semi-solid separation media include crosslinked polymer matrices such as poly(acrylamide/bis-acrylamide) and polymer solutions such as aqueous agarose. Polymer solutions, crosslinked polymer matrices, and hydrogels can all be used as separation media in embodiments of the present methods.

Immobilization of analytes within the separation channel can be carried out as desired, using any of the mechanisms described above or other available mechanisms. In some embodiments, the first capture agent or the second capture agent is a crosslinker, and immobilizing the analytes comprises crosslinking the analytes to the first surface or the second surface. Crosslinking can be effected by exposing the separation channel to UV light or another convenient stimulus. Alternatively or in addition, the first capture agent or the second capture agent can be an affinity structure, and immobilizing the analytes comprises binding the analytes to the affinity structure. Examples of affinity structures are provided above and include proteins (e.g., antibodies) and nucleic acids. The affinity structure can be coupled to the α first half-space or α second half-space as desired and can interact specifically and/or non-covalently with analytes of interest in the biological sample.

It will be recognized that embodiments of the methods employing two different capture agents in the two half-spaces allow differential probing of the biological sample. For example, when an antibody is used as the first capture agent and a crosslinker is used as the second capture agent, analytes can be immobilized both specifically and non-specifically in the same separation channel. When the first solid substrate is later moved relative to the second solid substrate, thereby moving apart the α half-spaces of the separation channel, immobilization of analytes in the biological sample can be compared in the two resulting detection channels.

Immobilization is effective to capture analytes in the separation medium that are in close proximity to the surfaces of the solid substrates. In some embodiments, the present devices are designed to have α half-spaces or separation channels with minimal widths, to increase the portion of analytes in a separation medium that can be immobilized. This portion also depends on the composition of the separation medium, the capture agents used in the separation channel, and other factors.

Some embodiments of the present methods further include removing the separation medium from the separation channel or detection channels after the immobilization step. For example, the separation medium can be removed by applying suction to an access port of the device, thereby withdrawing the separation medium from a channel in which it is retained, or driving fluid through an access port, thereby displacing the separation medium from the channel. In some embodiments, the separation medium is removed by applying complementary vacuum and pressure sources to two access ports located at opposite ends of the channel. The separation medium can be removed before or after the sliding step. In preferred embodiments, the mechanism used to remove the separation medium is gentle and does not strip analytes immobilized on the surfaces of the α half-spaces. For example, this mechanism does not introduce high shear forces or expose the α half-spaces to an aggressive chemical environment that causes immobilized analytes to detach.

In some embodiments, sliding one solid substrate with respect to the other can cleanly divide the separation medium remaining in a separation channel into two portions, where the portions correspond to the two α half-spaces from which the separation channel is formed. In other embodiments, however, such as when the separation medium is solid or semi-solid, sliding the substrates can cause fracturing of the separation medium or disruption of the interface at which the solid substrates meet. In these embodiments, it can be beneficial to remove the separation medium prior to sliding, or treat the separation medium so that it does not impede the movement of the solid substrates. For example, if the separation medium contains crosslinked polyacrylamide, it can be dissolved by treatment with perchloric acid and hydrogen peroxide, which can be introduced through one of the access ports of the device. Agarose gel media can be dissolved by heating and/or exposure to a chaotropic agent such as sodium iodide or guanidinium thiocyanate. Alternatively, the device can be disassembled to manually remove a solid separation medium from the α half-spaces in which was contained, and then reassembled for sliding and analyte detection. It will be recognized that any method used to remove the separation medium should not disturb analytes immobilized to the walls of the α half-spaces.

The sliding step can be performed as desired for the device being used, to align the α half-spaces with the β half-spaces in the α-β position described above. For example, if the α and β half-spaces in the two solid substrates are all linear and parallel to each other, then sliding can include moving one solid substrate relative to the other in a linear motion. This motion can be perpendicular or orthogonal to the long axis of each half-space or separation channel. Similarly, in some embodiments, the analytes are separated along a separation axis, and sliding the first solid substrate past the second solid substrate comprises moving the first solid substrate or the second solid substrate in a direction orthogonal to the separation axis. In embodiments employing the circular solid substrates described above, sliding can include rotating one solid substrate relative to the other. Sliding can be performed manually or automatically, for example with the aid of a motor.

In some embodiments, the present methods also include introducing a detection medium into the separation channel or detection channels for detecting the immobilized analytes. The detection medium can be introduced before or after sliding, and preferably after the separation medium has been removed. In some embodiments, the separation medium is removed after the immobilization step, and is displaced by the detection medium. Thus, the detection medium can be introduced at the same time that the separation medium is removed.

The detection medium can facilitate detection using color, fluorescence, chemiluminescence, radioactivity, or any other technology discussed above or available for use. The detection medium can include reagents appropriate for detecting analytes of the biological sample, and a carrier (for example, a buffered aqueous solution) that provides conditions compatible with detection using these reagents. In some embodiments, the detection medium includes a binding partner for one or more analytes. The binding partner can be a protein or nucleic acid, for example an antibody or labeled nucleic acid probe. Preferably, the binding partner binds to its target specifically, and if desired, multiple binding partners can be included in the detection medium to target multiple analytes. In some embodiments the detection medium further comprises a reagent that binds to or reacts with the binding partner. The reagent can be, for example, a secondary antibody or a chemiluminescent substrate.

The present methods thus allow analyte detection to occur in the slideable devices in a manner similar to western, Southern, or northern blotting. When protein analytes are immobilized in a detection channel, for example, a detection medium can be introduced that contains primary and secondary antibodies and an appropriate chemiluminescent substrate. Alternatively, when RNA or DNA is immobilized, the detection medium can contain a nucleic acid probe bearing a fluorescent label. Thus, proteins containing specific epitopes, or nucleic acids containing specific sequences can be conveniently detected. If desired, the detection medium can be added to a detection channel in multiple portions, for example to introduce a blocking agent or allow iterative antibody binding steps to occur.

Because sliding the solid substrates from the α-α position to the α-β position forms two detection channels from every separation channel, it will be recognized that two different sets of detection media and reagents can be used to detect analytes immobilized in the same separation channel. Thus, for example, proteins immobilized in one separation channel can be detected simultaneously with two different primary antibodies in separate detection channels after the sliding step. In some embodiments the same capture agent is disposed in the two α half-spaces of a separation channel, allowing for multiplexed detection of the same analyte(s) (or related analytes) in the two detection channels formed from these half-spaces. For example, the phosphorylated and unphosphorylated forms of a protein can both be captured on the walls of the α half-spaces forming a separation channel, using a crosslinker reactive with both forms. Sliding then forms an α-β detection channel and a β-α detection channel from these half-spaces, and the detection channels can be probed with different antibodies to distinguish between the phosphorylated and unphosphorylated forms of the protein.

Alternative embodiments of the methods can make use of two-layer devices with divided β half-spaces, as shown in FIGS. 7A-C. In these embodiments, analytes can be separated in α-α separation channels while the solid substrates are in the α-α position, and then dispensed into chambers of the β half-spaces upon sliding to the α-β position. The separation medium can be left in the separation channels after analyte separation and dispensed into the chambers along with the analytes. In some embodiments, one or more capture agents are disposed in the chambers of the divided β half-spaces, and analyte immobilization occurs after sliding the device and dispensing analytes into the chambers. Analyte immobilization can occur as desired or as discussed above, for example with a crosslinker. Detection can then occur by introducing a detection medium into the detection channels formed from the divided β half-spaces. In some embodiments, the detection medium is flowed into detection channels as described above. In other embodiments, additional half-spaces are filled with a detection medium, and are aligned with the divided β half-spaces by sliding the device an additional time, subsequent to analyte immobilization.

C. Systems

Any of the two-layer devices described herein can be part of a system for automatically separating and immobilizing analytes of a biological sample. In some embodiments, such a system includes the device, as well as a motor configured to drive the sliding movement of the first solid substrate past the second solid substrate, from the α-α position to the α-β position. Any convenient motor can be used, for example an electric motor. In some embodiments, the motor includes mechanisms to restrict the relative motion of the first and second solid substrates, or the positions at which such motion stops. These mechanisms can ensure, for example, that the solid substrates occupy only the α-α position and the α-β position, without stopping between these positions, and that the half-spaces forming the separation channels and detection channels (as discussed above) remain in register. The motor can be computer-controlled and can include software or firmware needed for its operation.

The present systems can also include, instead of or in addition to a motor, any apparatus needed to service the separation channels and/or detection channels of the device. For example, a system can include a vacuum source or pressure source coupled to at least one of the access ports, or a pair of electrodes disposed at opposite ends of a separation channel (e.g., in access ports). The system can also include any adapters, connectors, wires, tubing, or other ancillary apparatus useful for automating analyte separation, immobilization, and/or detection. When the system includes electrodes, it can also include a power supply configured to energize the electrodes to opposite polarities.

Systems can also include light sources useful for immobilizing analytes in the separation channels (such as by photo-crosslinking) of a two-layer device, or for detecting analytes in the detection channels (such as by fluorescence). In some embodiments, a system includes a UV and/or visible light source configured to direct light into the separation channels or the detection channels. Instead or in addition, the system can include a detector configured to detect light emitted from the detection channels. Examples of suitable light sources and detectors are provided above. In some embodiments, the light source or detector is provided along with optics such as lenses or mirrors. The light source and/or detector can be configured in concert with the device to provide or detect light having characteristics (e.g., wavelength, intensity, polarization, or collimation) used in the end-user's chosen detection scheme.

D. Kits

The two-layer devices described herein can also be provided as kits for separating and detecting analytes of a biological sample. A kit can include a device along with a separation medium or detection medium, as described above. Kits can also include other apparatus for operating the devices.

V. Three-Layer Devices

Figure 8:
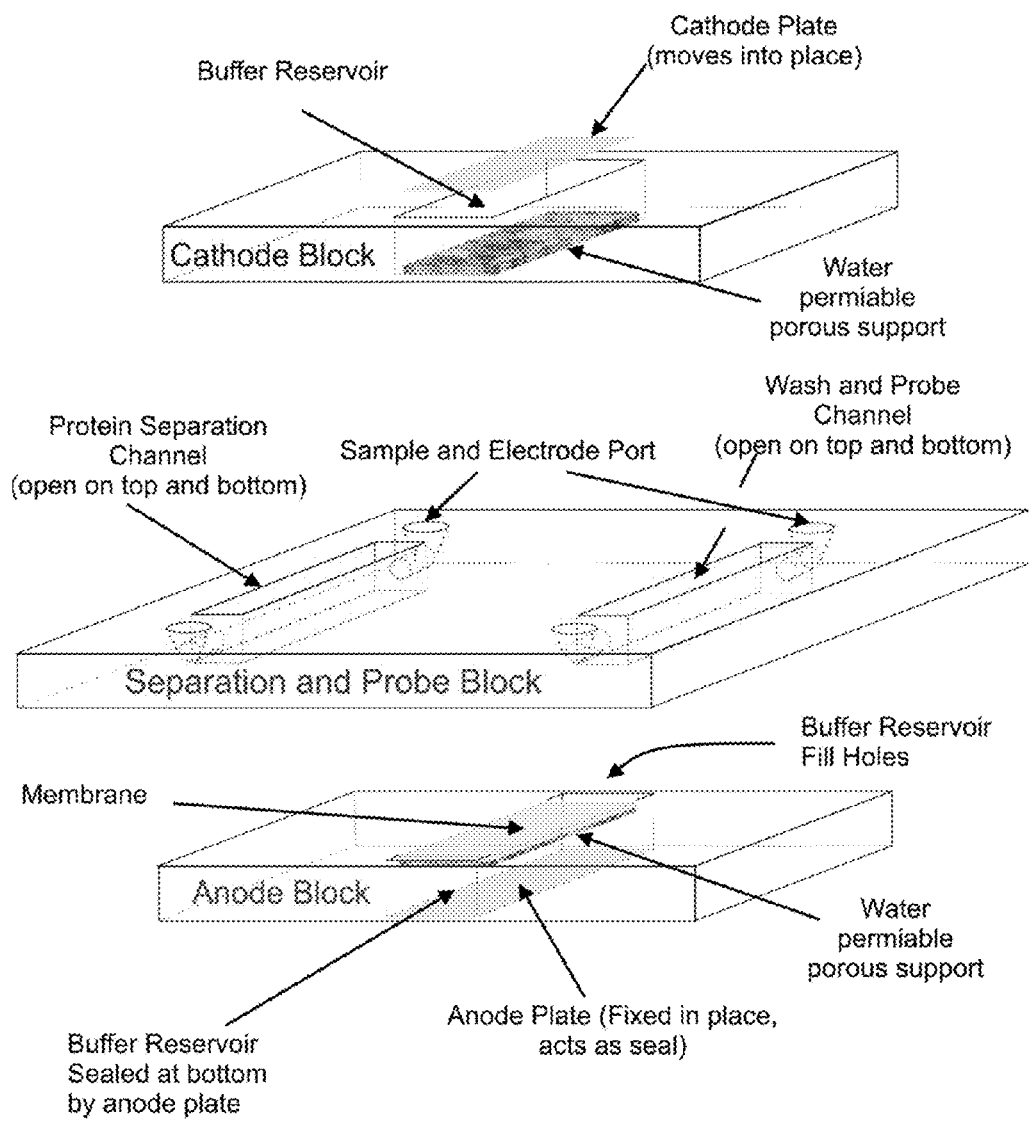
FIG. 8 is an exploded view of a three-layer device according to some embodiments of the present invention. The three layers of the device are shown prior to assembly. As shown, the middle layer is thicker than the top and bottom layers, and contains access ports and through-slits. One through-slit in the middle layer defines a separation channel, and the other through-slit defines a detection channel. Each of the top and bottom layers also contains a through-slit or indentation to permit transfer of analytes to the membrane, which is disposed in the bottom layer. The membrane rests on a porous support.

The present devices also include slideable blotting devices constructed from three or more layers of a suitable solid substrate, such as glass or plastic as described above (FIG. 8). The layers are held in tight association and include channels formed from indentations or through-slits. A separation channel in the middle layer of the device is first used for separation of analytes in a biological sample. The analytes can be proteins or nucleic acids, for example. Subsequently, sliding one or more of the layers with respect to the other layers results in the alignment of the separation channel with a membrane (for example, a porous binding surface or material such as nitrocellulose or polyvinylidene fluoride), permitting the orthogonal transfer of the biomolecules from the separation channel to a capture surface on the membrane. Detection of at least one targeted analyte from the separated biological sample can then occur. The device can be used in any blotting procedure involving biomolecules, for example western blotting or nucleic acid (northern or Southern) blotting. The device can also be part of a system and/or instrument to perform and control analyte separation (using, for example, a power supply, electrodes, or pressure or vacuum sources), move and align the layers, transfer analytes to the membrane (including fluid control), process the membrane, and detect analytes (using visible light, fluorescence, chemiluminescence, mass spec or other means). Such a system can include software or firmware control. Kits containing the device, as well as buffers and solutions required to perform analyte separation and detection using the device, are also provided.

A. Device Structure

In some embodiments, the present devices include three layers, which for convenience are referred to herein as the top layer (or alternatively, "layer 1"), the middle layer ("layer 2"), and the bottom layer ("layer 3"). Each layer comprises a solid substrate made of any desired materials, such as plastic, metal, glass, or ceramic. The solid substrates can have any of the characteristics recited above for two-layer devices; for example, in some embodiments, each substrate is impervious to liquids. The layers are planar and in contact with each other such that the middle layer is sandwiched between the top layer and the bottom layer. In other words, a top surface of the middle layer is in contact with the top layer, and a bottom surface of the middle layer is in contact with the bottom layer. In some embodiments, the surfaces of the layers are flat and/or configured to reduce friction resulting from translation of one layer relative to another. The middle layer is configured to slide relative to the top layer and/or the bottom layer to facilitate the blotting of analytes.

A three-layer device can also include one or more indentations or through-slits in each layer, in the faces of the layers that are in contact with each other. For example, a through-slit in the top layer can provide a passage between the space above the top layer and the interface between the top layer and middle layer. A through-slit in the middle layer can provide a passage between the top and bottom surfaces of the middle layer, and thus between the interfaces of the middle layer with the adjacent layers above and below. While a through-slit penetrates all the way through the layer in which it is disposed, an indentation can occur on only one surface of a layer. For example, an indentation in the top layer can provide a cavity between the top layer and middle layer. Any desired number of indentations or through-slits can be established in each layer of the device.

In some embodiments, the device includes a separation channel defined by a through-slit in the middle layer. The separation channel is configured to accommodate a separation medium, as well as a biological sample applied to the separation medium, and serves as the location in the device where analyte separation can occur. The separation channel can have any desired dimensions, and in some embodiments has a long axis (or "separation axis") along which analyte separation occurs, for example using electrophoresis. The separation channel can be bounded on the top and bottom by surfaces of the top layer and/or bottom layer, respectively, when these layers are appropriately aligned with the middle layer.

A three-layer device can further include a plurality of access ports. The access ports can be similar to those discussed above for two-layer devices, and can comprise holes, cavities, or passages in one or more layers of the device. In some embodiments, the device includes a pair of access ports configured to supply materials or electrical current to opposite ends of the separation channel. The access ports can be disposed in any convenient layer of the device, such as the top layer or the middle layer, and can be in fluidic communication with the separation channel. In some embodiments, at least one access port is coupled to a vacuum source or a pressure source, and can be used, for example, to fill the separation channel with a separation medium, load a sample onto the separation medium, or evacuate the channel after separation. In some embodiments, at least one access port is aligned with a separation electrode. The electrode can be positioned near the access port, to deliver electrical current to the separation channel in an appropriate configuration of the device, or can be disposed directly in the access port. The same access port(s) can be used to supply materials and electrical current, or separate, specialized access ports can be installed in the device for each purpose. In some embodiments, at least one access port has a tapered cross-section that varies in area in proportion to the distance from the separation channel. Thus, the access port is narrower at an end closer to the separation channel. The tapering can be beneficial to, e.g., prevent bubble formation or focus the flow of materials or electrical current into the separation channel.

The device can further include a membrane disposed in a through-slit of either the top layer or the bottom layer. The membrane can be aligned with the separation channel when the through-slits associated with the membrane and separation channel are aligned with each other. Such alignment can be achieved by sliding the middle layer of the device relative to the top layer or the bottom layer. The membrane can be positioned to receive and immobilize analytes of the sample that have been separated in the separation channel. As discussed below, blotting electrodes can be accommodated in the top layer and bottom layer of the device, for example behind the membrane and across the separation channel from the membrane, to facilitate electroblotting.

The geometry and mechanics of the device can be engineered to optimize aspects of analyte separation or blotting. For example, in some embodiments a through-slit of the top layer is aligned with a through-slit of the bottom layer, such that both through-slits can be simultaneously aligned with the separation channel. This alignment can be established permanently, by constraining the sliding movement of the top layer relative to the bottom layer, or can be established in certain slideable configurations of the device used for electroblotting. The alignment of through-slits in the top and bottom layers can allow blotting electrodes disposed in these through-slits to establish an electrical potential across the separation channel. In some embodiments, the through-slits in the top layer, middle layer, and bottom layer have approximately equal cross-sectional areas. Here, cross-sectional area is measured in the plane of each layer, when viewed from above or below the device. This configuration allows the full area of the separation channel to be disposed between the blotting electrodes during electroblotting, and analytes from all areas of the separation medium to be transferred to the membrane. In some embodiments, the through-slit of the top layer, middle layer, or bottom layer comprises angled walls configured to allow air bubbles to escape. Such bubbles can interfere with analyte separation or blotting.

Similarly, the placement or dimensions of the membrane in the device can be chosen to optimize blotting. In some embodiments, the membrane is flush with a surface of the top layer or the bottom layer, the surface being in contact with the middle layer. When flush with this surface, the membrane can be in direct or nearly direct contact with the separation medium upon alignment of the through-slits containing the separation channel and membrane. Thus, analytes can be efficiently transferred from the separation medium to the membrane. In some embodiments, the membrane spans the full cross-sectional area of the through-slit in which it is disposed. This configuration prevents electrical current from the blotting electrodes, or analytes migrating under the influence of this current, from passing around the membrane during blotting. Thus, the amount of analytes capture on the membrane is maximized. If desired, the membrane can be affixed to the top layer or the bottom layer of the device with a fluid-tight seal, to further ensure that current passes through the membrane. A seal can also prevent the separation medium from being exposed to fluids in through-slits of the top layer or bottom layer, and thus prevent the formation of pH or concentration gradients that can interfere with blotting. The membrane can be attached to a layer of the device as desired, for example with an adhesive or sonic or thermal welding.

As in the two-layer devices described above, the layers of the three-layer devices are configured to slide past each other along the interfaces between these layers. Any desired mechanisms can be used to facilitate sliding. For example, wheels or rails can be employed as discussed above. In some embodiments, a surface of the top layer or bottom layer in contact with the middle layer is coated with a lubricant. The lubricant can reduce the amount of friction or friction-induced heating resulting from the sliding motion, and minimize the forces needed to carry out sliding. The lubricant can be an inert oil, for example, which can remain phase-separated from any aqueous media containing biological analytes, and thus not interfere with separation or blotting of these analytes. Examples of suitable inert oils include various mineral oils. Independently or as a result of the lubricant, a surface of the top layer or bottom layer in contact with the middle layer can be hydrophobic. This surface can be made hydrophobic by applying an appropriate surface treatment or coating, such as Teflon. Hydrophobic surfaces can prevent aqueous solutions (including separation media and detection media) used in handling biological analytes from leaking out of through-slits or indentations of the device at the interfaces between layers. Other methods of preventing such leaking, for example by placing rubber gaskets around the separation channel or the membrane used in blotting, can be used instead or in addition. In some embodiments, the middle layer of the device contacts the top layer or the bottom layer through a fluid-tight interface, such that when the separation channel is enclosed by a solid surface of the top layer or the bottom layer, fluid accommodated in the separation channel cannot escape the separation channel through the interface.

Once immobilized on a membrane using one of the present three-layer devices, analytes can be detected as desired, for example using one of the methods described above. In some embodiments, analytes are detected optically, using color, fluorescence, or chemiluminescence. Accordingly, the layers of the device can be configured to allow light of desired wavelengths to pass through. In some embodiments, the top layer, the middle layer, or the bottom layer is transparent to UV and/or visible light. In some embodiments, the top layer, the middle layer, and the bottom layer are all transparent to UV and/or visible light. These embodiments are all consistent with light originating from outside or inside the device. Accordingly, light can pass through one or more layers of the device and be incident on analytes, for example to cause fluorescence excitation, or can emitted by the analytes, for example by chemiluminescence, and then be detected after passing through one or more layers. Transparent solid substrate layers can allow analytes to be detected after blotting while the membrane is still disposed in one of the through-slits of the device.

The device and the layers thereof can be dimensioned as desired. In some embodiments, the middle layer is wider than each of the top and bottom layers in a dimension parallel to the direction in which the layers are configured to slide. These embodiments allow many parallel separation channels to be disposed in the middle layer for multiplexed sample handling. Analytes can be separated in each separation channel independently (or if desired, simultaneously), and then the layers of the device can be shifted to align the separation channels with through-slits in the top or bottom layer containing membranes. In some embodiments, the middle layer is wider than each of the top and bottom layers in a dimension parallel to the separation channel. This configuration allows access ports to be disposed in the middle layer, adjacent to the separation channel, and remain coupled to other parts of the device (for example, pressure sources, vacuum sources, or electrodes) regardless of the position of the top and/or bottom layer. The device can also include a clamp configured to hold the top layer, middle layer, and bottom layer together. The device can be mechanically coupled to the top layer, middle layer, and/or bottom layer as desired.

The present three-layer devices can further include blotting electrodes. In some embodiments, a device includes a pair of blotting electrodes, wherein a first blotting electrode is disposed in a through-slit of the top layer, and a second blotting electrode is disposed in a through-slit of the bottom layer. The first or second blotting electrode can serve as a cathode, and the other blotting electrode can serve as an anode, as desired. Either the first or the second blotting electrode can be disposed in the same through-slit as the membrane, on the opposite side of the membrane from the middle layer. Thus positioned, the electrodes can be used to facilitate the transfer of analytes from the separation channel in the middle layer to the membrane disposed in the top layer or the bottom layer, when the layers are appropriately aligned. The blotting electrodes are preferably oriented along a different axis from any electrodes associated with the separation channel (i.e., separation electrodes) so that an electric field between the blotting electrodes is orthogonal to an electric field between the separation electrodes, and analytes migrate in orthogonal directions for separation and blotting. The blotting electrodes can be of typical configurations such as plates, wires, or pins, coated or deposited as one or more layers onto surfaces or structures. Blotting electrodes can be made of standard materials such as copper, platinum, brass, silver, gold, titanium, graphene, carbon, stainless steel, mixed metal oxides, indium tin oxide, and iridium. Alternatively, the blotting electrodes can be conductive polymer electrodes, as described in co-assigned U.S. Provisional Application No. 62/114,387 (incorporated herein by reference). If desired, one or both of the blotting electrodes can be disposed in an indentation in the top or bottom layer, rather than a through-slit. An indentation can provide better sealing of the separation channel in some cases, and does not hinder immobilization or detection of analytes, especially when the indentation is not disposed in the same layer of the device as the membrane.

In some embodiments, a porous support is disposed in either the top layer or the bottom layer of the device, between the membrane and the blotting electrode in that layer. Suitable porous supports can be prepared from sponge, paper (e.g., Whatman paper), ceramic, or plastic (using, for example, polyethylene, polypropylene, or polytetrafluoroethylene) among other materials. In some embodiments, the porous support can absorb liquids, particularly aqueous solutions. The porous support can prevent direct contact between the membrane and the closest blotting electrode, and prevent any ions, radical species, or gasses formed at the electrode from interfering with immobilization of analytes on the membrane. Porous supports can generally be installed in through-slits of the device, for example in the top layer and/or the bottom layer, to provide structural support to elements such as the membrane or the blotting electrodes.

The device can further include a detection channel, which can occur in the middle layer, for example adjacent to the separation channel. In some embodiments, the detection channel is defined by an additional through-slit in the middle layer of the device, and can be aligned with the membrane used for blotting by sliding the middle layer relative to the top layer or the bottom layer. Thus, the process for separating and detecting analytes can include two sliding steps, first to align the separation channel with the membrane, and then to align the membrane with the detection channel. The device can include one or more access ports, in addition to those servicing the separation channel, to service the detection channel. An additional access port can be configured to supply materials to the detection channel or remove materials from the detection channel. Thus, detection reagents such as antibodies or nucleic acid probes can be flowed through the additional access port(s) into the detection channel, where they can contact analytes immobilized on the membrane.

In some embodiments, the middle layer of a three-layer device includes a plurality of through-slits defining a plurality of separation channels for multiplexed sample processing. For example, the middle layer can include at least 12, 20, 26, 48, or 96 through-slits. Each separation channel can be associated with one or more access ports (including, for example, one or more electrodes) to facilitate analyte separation. Each separation channel can also be associated with a distinct through-slit in the top or bottom layer to accommodate a membrane, and in some embodiments through-slits in both the top and bottom layers to accommodate blotting electrodes. The plurality of through-slits in the middle layer of the device can also define a plurality of detection channels. In some embodiments, there is one detection channel per separation channel, or each separation channel is adjacent to a detection channel. In some embodiments, the separation channels are all oriented parallel to each other (for example, along a separation axis), and/or each separation channel is parallel to the adjacent detection channel. Multiplexed sample processing allows steps such as analyte separation, blotting, and detection to be performed rapidly for many samples, and allows each sample to be treated independently (for example using a unique set of detection reagents in the detection step).

B. Methods

The three-layer slideable devices described above can be used to separate and blot analytes of a biological sample. The present methods involve loading the sample in the separation channel; supplying current to opposite ends of the separation channel through the access ports, thereby separating analytes of the sample along the length of the separation channel; sliding the middle layer relative to the top layer or the bottom layer, thereby aligning the membrane with the separation channel; and transferring the analytes from the separation channel to the membrane.

In some embodiments, separation of the analytes occurs when a separation medium is disposed in the separation channel. Any desired separation medium can be used, and examples of separation media are provided above. The separation medium can be introduced into the separation channel using the techniques discussed above for two-layer devices. For example, depending on its composition, the separation medium can be flowed through an access port into the separation channel and optionally allowed to polymerize or solidify. The sample can be introduced into the separation channel along with the separation medium (for example, when the sample is suspended in the separation medium), or can be loaded into or onto the separation medium after the separation medium has already been introduced into the device. In some embodiments, the sample is loaded through one of the access ports.

Analytes of a sample can be separated in the device as desired, using electrophoresis, electroosmosis, or isoelectric focusing, as described above (FIG. 9). In these techniques, current is supplied to opposite ends of the separation channel through the access ports, for example using electrodes connected to a power supply.

Figure 10:
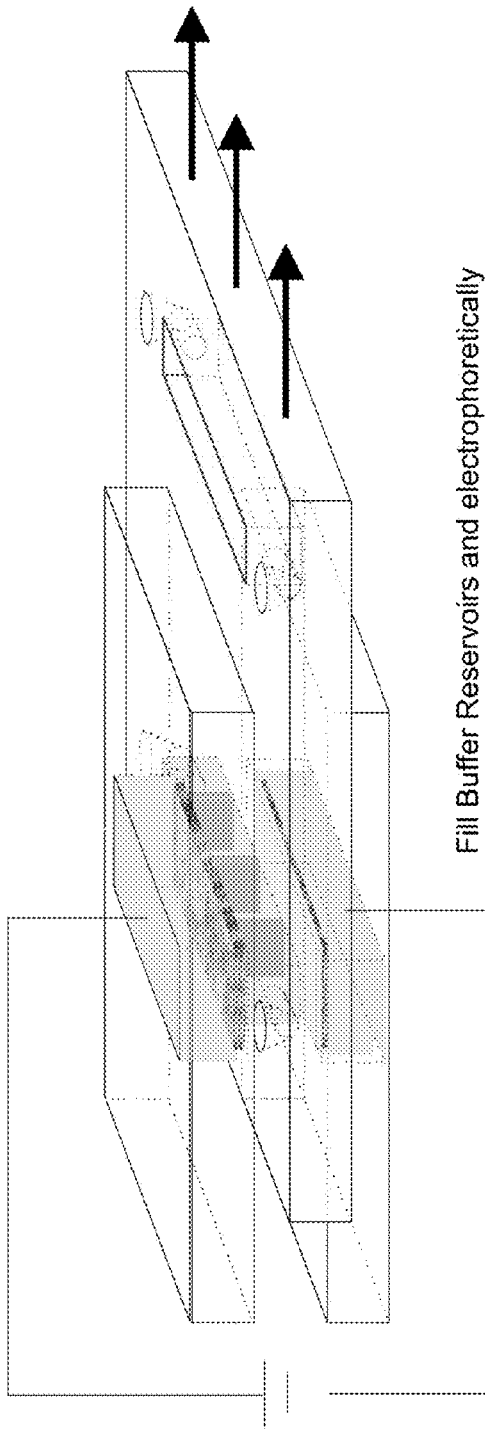
FIG. 10 shows protein transfer using embodiments of the three-layer devices and methods described herein. The separation channel is shown aligned with through-slits in the top and bottom layers of the device after sliding the middle layer relative to the other layers. A membrane is disposed in a through-slit in the bottom layer. The device is submerged or otherwise engaged to buffer on both the top and bottom, and electrodes (cathode top, anode at bottom) are inserted and activated to perform the electrophoretic transfer of the proteins from the separation channel to the membrane.

The sliding step preferably occurs after analytes of the sample are separated in the separation channel (FIG. 10). Thus, the membrane does not come into contact with the analytes and any separation medium until the analytes are positioned in the channel for blotting, and detection background is reduced. Accordingly, the separation channel can be offset from the through-slit in the top layer or the bottom layer prior to sliding. To achieve sliding, force can be applied to the top layer, the middle layer, or the bottom layer of the device. In some embodiments, the middle layer moves in a direction relative to the top layer or the bottom layer that is perpendicular to the length of the separation channel. Sliding can be performed manually or automatically.

In some embodiments of the methods, blotting electrodes are disposed in through-slits of the top layer and the bottom layer, and transferring analytes from the separation channel to the membrane includes energizing the electrodes to opposite polarities. Any appropriate voltage or current can be used in this step, and electrotransfer can occur in a wet, dry, or semi-dry format as discussed above. In some embodiments, transferring the analytes to the membrane requires filling one or both of the through-slits containing the blotting electrodes with buffer. For example, the through-slit containing one blotting electrode and the membrane can be filled with buffer, the through-slit containing one blotting electrode but not containing the membrane can be filled with buffer, or both through-slits can be filled with buffer. The buffer can be introduced by applying sponges or other absorbant materials to one or both of the through-slits, or by submerging the device in buffer. The same buffer can be introduced into the through-slits in the top and bottom layers, or different buffers can be introduced. Any buffer or buffers with appropriate pH, salt concentration, and/or buffering capacity for electrotransfer can be used in this step.

The present methods can also include detecting analytes on the membrane. In some embodiments, the analytes are immobilized on the membrane or have been deposited there in the transfer step. To perform detection, the membrane can be removed from the device and/or the device can be disassembled. The membrane can then be exposed to detection reagents, such as antibodies or nucleic acid probes, as in conventional electroblotting procedures. Alternatively, the membrane can be processed in situ within the device. In some embodiments, for example, the device further includes a detection channel as described above, where the detection channel is defined by a through-slit in the middle layer.

Figure 11:
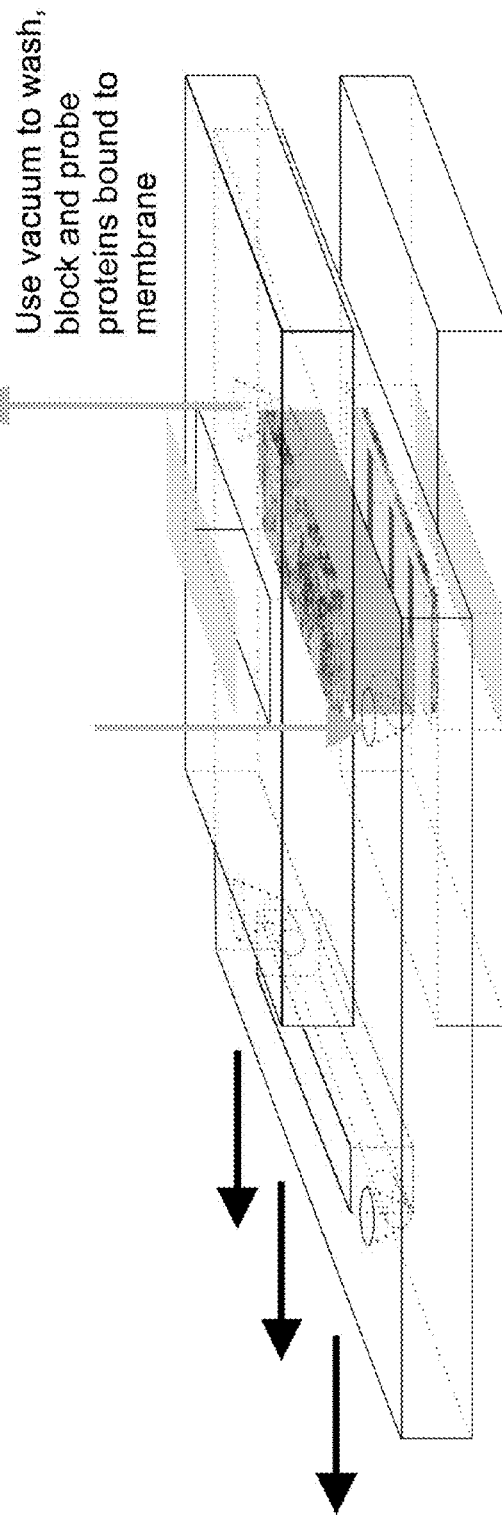
FIG. 11 shows membrane blocking, washing and probing using embodiments of the three-layer devices and methods described herein. Shown is the alignment of the detection channel to the membrane after sliding the middle layer to the left (opposite the direction of sliding shown in FIG. 10). The top layer is shown to stay fixed relative to the middle layer, but in other embodiments the top layer can move opposite the middle layer, creating a solid top surface for the detection channel rather than the porous sheet as shown. The device can be removed from the transfer solution and the solution removed from the slits prior to the translation step occurring. Detection reagents are introduced through access ports adjacent to the detection channel shown using pressure, a vacuum, or capillary action. An instrument can control aspects of operation of the device, such as flow rates or incubation times, to afford the most sensitive detection of a target analyte. Detected analytes can be imaged from within the device.

Detecting the analytes on the membrane can include sliding the middle layer of the device relative to the top layer or the bottom layer, thereby aligning the membrane with the detection channel (FIG. 11). Detection reagents or a detection medium can then be flowed through the detection channel as described above for the two-layer device. Detection can be performed optically, for example using color, fluorescence, or chemiluminescence, as described above.

Any sliding step for detection is additional to that performed after analyte separation, and can result in a configuration of the device distinct from those observed immediately before and after analyte separation. In some embodiments, sliding occurs in opposite directions after analyte separation and after analyte transfer (i.e., for detection). For example, the middle layer of the device can be slid in a first direction relative to the top layer or the bottom layer to align the membrane with the separation channel, and subsequently slid in a second direction relative to the top layer or the bottom layer to align the membrane with the detection channel, the first direction being the opposite of the second direction.

If desired, after completion of the method, the device can be reconditioned for subsequent or repeated use. For example, the separation medium can be removed from the separation channel, a new separation medium can be introduced, and the membrane disposed in a through-slit of the top layer or bottom layer can be replaced. It will also be recognized that the present methods can be extended to multiplexed embodiments of the three-layer device. For example, separation of analytes from multiple samples can be performed simultaneously in multiple separation channels, and these analytes can then be transferred to membranes and detected, with a distinct membrane for each separation channel. A different set of detection reagents can also be used to detect the analytes on each membrane.

C. Systems

Any of the three-layer devices described herein can be part of a system for automatically separating and blotting analytes of a biological sample. In some embodiments, such a system includes the device, as well as a motor configured to drive the sliding movement of the middle layer relative to the top layer and/or the bottom layer. Any convenient motor can be used, for example an electric motor. In some embodiments, the motor includes mechanisms to restrict the relative motion of the layers, or the positions at which such motion stops. These mechanisms can ensure, for example, that the separation channel is offset from the membrane during analyte separation, and aligns closely with the membrane prior to analyte transfer. The mechanisms can also ensure that the membrane aligns closely with the detection channel, if any, after analyte transfer and prior to introducing detection reagents. Finally, the motor mechanisms can ensure that an appropriate amount of force or pressure is applied to the layers of the device to keep them in close contact and prevent liquids from escaping from through-slits in one or more of the layers. The motor can be computer-controlled and can include software or firmware needed for its operation.

The present systems can also include, instead of or in addition to a motor, any apparatus needed to carry out analyte separation and/or blotting. For example, a system can include a pair of separation electrodes disposed at opposite ends of the separation channel, and a power supply configured to energize the electrodes to opposite polarities. A system can also include a pair of blotting electrodes, one disposed in a through-slit of the top layer and the other disposed in a through-slit of the bottom layer, wherein one blotting electrode of the pair is disposed in the same through-slit as the membrane, on the opposite side of the membrane from the middle layer. Such a system can further include a power supply configured to energize the blotting electrodes to opposite polarities. Any appropriate power supplies can be included in the systems, along with wires, electrical adapters, and/or controllers.

Systems can also include light sources useful for illuminating and detecting analytes immobilized on the blotting membrane. For example, the light source can be used to illuminate fluorescent analytes or fluorescent binding partners for the analytes. The light source can also be used to visualize analytes during separation in the separation channel. Accordingly, in some embodiments, a system includes a UV and/or visible light source configured to illuminate the separation channel or membrane. Instead or in addition, the system can include a detector configured to detect light emitted from the separation channel or membrane. Examples of suitable light sources and detectors are provided above. In some embodiments, the light source or detector is provided along with optics such as lenses or mirrors. The light source and/or detector can be configured in concert with the device to provide or detect light having characteristics (e.g., wavelength, intensity, polarization, or collimation) used in the end-user's chosen detection scheme.

Furthermore, the present systems can include any apparatus needed to service the separation channel of the device. For example, a system can include a fluid handling subsystem configured to deliver or remove fluid to or from the separation channel, wherein the fluid handling subsystem connects to the access ports. The fluid handling system can include a vacuum source or a pressure source, for example. In some embodiments, the fluid handling subsystem is used to introduce a separation medium into the separation channel and/or load the sample containing analytes to be separated. The system can also include any adapters, connectors, wires, tubing, or other ancillary apparatus useful for automating analyte separation.

D. Kits

The three-layer devices described herein can also be provided as kits for separating and blotting analytes of a biological sample. In some embodiments, a kit includes a device as well as a plurality of replacement membranes. Any of these membranes can replace the membrane initially installed in the device as well as replacement membranes used subsequently. In these embodiments, the membrane of the device is configured to be replaced after use, for example by removing the membrane from the through-slit in the top or bottom layer in which it is disposed. A kit can also include a device along with a separation medium or detection reagent, as described above.

VI. Examples

A. Example 1.

Automated Blotting in a Two-Layer Device

This example describes embodiments of the invention based on predicted results rather than results actually achieved. An automated blotting method using a two-layer device is performed in steps, as described below.

Provided are methods and compositions involving the use of two opposing microfluidic half-spaces to form enclosed (and variable) microfluidic channels. The channels are created by moving one or both half-spaces in relation to one-another, to conduct an automated SDS-PAGE and Western Blot-like immunoassay. The method can be described in five steps and is illustrated in FIGS. 1-6.

Step #1. Two dissimilar solid substrates with open microfluidic channels on their faces are placed in intimate contact with one another. Alignment of the two solids creates unique channels where liquid can be introduced and contained within a newly created microfluidic channel. In the first step, a single channel is created in the device and within this channel a protein sieving polymer matrix (e.g., a "separation medium") is introduced. This sieving matrix is used to separate proteins using SDS-PAGE. The sieving matrix is considered to be a liquid polymer in some embodiments.

Step #2. After application of a sample and subsequent analyte (e.g., protein) separation, the analytes that are within closest approach to the walls of the microfluidic channel are immobilized (e.g., covalently fixed) to the wall. Covalent linkage can occur through a number of processes. In some embodiments, a UV photo-activatable benzophenone is used to crosslink proteins to the wall. The benzophenone is covalently linked to the walls of the device prior to SDS-PAGE. After cross-linking the analyte (e.g., protein) to the wall, the analyte (e.g., protein) liquid sieving matrix (and non-crosslinked analyte) is removed from the channel (pressure), leaving behind the analytes which are covalently attached to the wall.

Step #3. The two fluidic half-spaces are moved/sheared in relation to one-another, to create two new fluid paths. Each new (and unique) fluid path contains one half of the fluidic channel used for analyte (e.g., protein) separation and a new channel half-space (not involved with separation).

Step #4. In at least one of the new fluid paths, all the components of a standard diffusion-based western blot assay are introduced. For example: blocking buffer, antibodies (primary and secondary) and washing buffer.

Step #5. Detection of the target analytes (e.g., proteins) are viewed by chemi-luminescence or fluorescence of the antibodies, via an appropriate excitation and emission optical system. In some embodiments, the chips are transparent to light from ultraviolet and visible sources.

In some embodiments, the order of steps can be reversed such that Step #3 occurs before Step #2. In some of such embodiments, after analyte separation in the separation medium, the chip translation occurs to fractionate/dispense portions of matrix containing the separated analytes into smaller cavities/wells/chambers, while maintaining the sizing or separation of analytes (see, e.g., FIG. 7). In some embodiments, a zig-zag pattern of the wells/cavities/chambers along the separation axis allows for all regions along the separation dimension to be sampled. The size and number of the cavities can be used to control the separation resolution. Additionally, the zig-zag well pattern can be repeated multiple times to make more copies of the fractionated separation allowing for multiplex detection.

Once the slipping action has completed, then the analytes can be immobilized to the well/cavity surface and detection can be performed as described. Further slipping of the chip could then position a flow channel above each set of zig-zag wells allowing for probing of different analytes (i.e., multiplex detection).

B. Example 2.

Automated Blotting in a Three-Layer Device

This example describes embodiments of the invention based on predicted results rather than results actually achieved. An automated blotting method using a three-layer device is performed in steps, as described below.

The three layers of the device are assembled such that the access ports in the top layer (layer 1) align with the slits in the middle layer (layer 2). The slits in the two outside layers (layers 1 and 3) are offset from those in the middle, effectively creating channels in the middle layer where the top and bottom faces are derived from the solid portions of the two outer layers (i.e. regions between the slits of the outer layers 1 and 3). The device layers are clamped together in a device holder.

In some embodiments, the device and system are used to perform Western blotting. In this case, one or more channels in the middle layer are first filled with a polymer matrix, or acrylamide solution that upon polymerization creates a crosslinked gel within the channel(s), thus creating an array of gel strips. In the case of a crosslinked gel, the device can be part of kit where the crosslinked gel strips are precast in the device and the user does not need to prepare the gels before performing the assay. The device holder applies sufficient force combined with the surface treatments of the device so that the introduced solutions remain isolated in the channels and do not migrate to adjacent channels.

Figure 9:
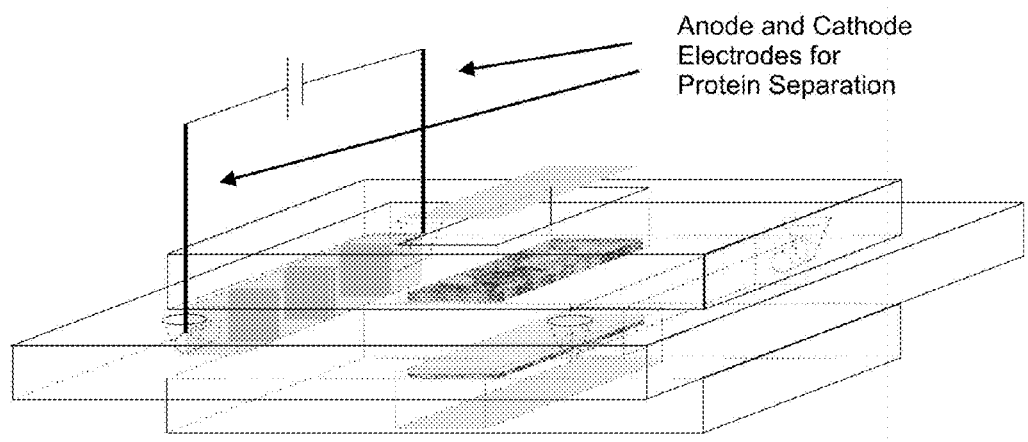
FIG. 9 shows protein separation using embodiments of the three-layer devices and methods described herein. A separation channel containing a hydrogel, like polyacrylamide, is shown on the left. The sample is loaded into one access port and electrodes are then inserted into the access ports to perform electrophoretic separation of the proteins (e.g., SDS-PAGE). The separated proteins are shown as pink bands. The position of the membrane in the bottom layer and other channels, slits, and port to be used for analyte transfer and detection steps are also shown.

In the next step, a biological sample, suspended and heated in an appropriate sample buffer (e.g, an SDS-PAGE sample buffer), is loaded into one of the access ports. Electrodes aligned to the access port positions are interfaced with the ports and an electric current is applied across the channel, effectively driving the separation of the analytes in the gel or polymer in the channels (FIG. 9).

Once the separation has completed, layers 1 and 3 of the device are slid relative to layer 2, such that the slit in layer 1 aligns with the channel containing the separation medium in layer 2, and the membrane and slit in layer 3 likewise align with the separation medium. The net result of this sliding event is that a flow path is created from the outside of the top face through all 3 layers to the outer face of the bottom layer (FIG. 10).

The entire device can then be submerged in transfer buffer, or after the sliding has occurred, a transfer buffer can be applied to the slit in layer 1 and the chip rested above a reservoir of transfer buffer such that the slits in the bottom layer are filled with buffer completing an uninterrupted flow path. In some embodiments, the slits in the top and bottom layers contain features that facilitate the easy introduction of transfer buffer without the accumulation of bubbles, such as a pathway for air to escape or angled walls. A second set of electrodes can then interface with the top slit and below the device to effect the transfer of the separated analytes to the membrane or porous support similar to a conventional western blotting process. In some embodiments, the reduced thickness of the separation medium facilitates faster and more effective transfer of analytes of all size compared to traditional western blotting. In some embodiments the shape, position or introduction of other features can be used in the lower buffer reservoir to prevent bubbles from accumulating in the slits of the lower layer. In other embodiments, the transfer step can be performed with the device in a vertical rather than horizontal position. The vertical position is more similar to the position of a conventional gel in a standard tank blotting process and prevents bubbles from accumulating in the slits outside of the separation zone.

Once the transfer step has completed, in some embodiments, the middle and top layers are slid a second time, for example in opposing directions, to align another empty slit above the membrane (middle layer), as well as fresh access ports in the top or middle layer to the position of the membrane. Detection reagents such as blocking solutions, wash buffers, primary antibodies, secondary antibodies, and detection substrates can all be introduced in succession through the access ports using pressure or a vacuum to probe the membrane surface for the identification of specific target(s) like in the standard Western blotting workflow (FIG. 11).

Once the detection step has been performed, the device can be imaged using suitable optical means (such as a CMOS or CCD detector), or electronic, radioactive, IR, or other means to identify the position, intensity, color, or other attributes of the detected target(s). The instrument can have a suitable excitation and emission optical system including a light source and filters. In the cases of fluorescent, chemiluminescent, or chromogenic detection, the device can be transparent or transmissive to desired wavelengths of light, for example UV, visible, or IR light. The instrument software and/or firmware can then perform analysis of the resulting signals to quantitate amounts, determine size, etc. Application of a standard to one or more of the channels can be used to normalize the results to a ladder. Internal standards in each sample can be used to align/normalize results across channels.

C. Example 3.

Variations on Automated Blotting in a Three-Layer Device

This example describes embodiments of the invention based on predicted results rather than results actually achieved. Variations on the automated blotting method presented in Example 2 are described below.

In some embodiments, the membrane or support can be made of PVDF. In these embodiments, before the separation region is slid adjacent to the membrane, the membrane might require wetting with alcohol and equilibration with buffer. This can be accomplished by aligning the detection channel to the membrane prior to beginning the process, or the layer containing the membrane can be prepared first prior to assembly of the stacked device.

Blotting procedures in addition to Western blotting are possible using the present devices and methods. For example, nucleic acids can be separated and probed once bound to a membrane or other porous support. Additionally, biomolecules can be separated by iso-electric focusing (IEF) instead of SDS-PAGE to identify similar molecules having different pIs or to detect molecules with differences in post-translational modifications. Molecules can be separated via a resin or monolith such as with chromatography and then transferred to the porous support for detection. In some cases, the analytes captured on the porous support are subsequently eluted for analysis by downstream methods such as mass spec. The bottom layer can also be made such that it can be removed and interface directly with downstream methods. The separation channel can be designed for the arraying of cells in a hydrogel, such that sliding allows one to lyse the cells and effect the transfer of their contents (for example, proteins or nucleic acids) to the porous support for subsequent probing.

The device shown in FIGS. 8-11 has a single separation channel and a single detection channel. However, a device as described herein can have any desired number of separation/detection units, such as 10, 12, 20, 26, 48, or 96, so that multiple samples can be simultaneously analyzed. The number of such units is limited only by factors such as the chosen footprint, channel dimensions, permissible pitch between units, and assay sensitivity. The position/pitch of access ports in such devices can be set to allow use of multichannel pipets for ease of use.

Multiple targets can also be detected in a single channel, allowing for multiplexing (for example, RGB for fluorescent tags). Multiple probing channels of lesser width can also be interfaced to a single membrane/porous substrate capture zone.

Devices as described herein can be disposable or single use in nature. Alternatively, devices can be made of materials that allow for cleaning and reuse, except for the membrane layer. Some embodiments use more than 3 layers to incorporate additional functionality, or fewer than three layers (e.g., two layers), where the separation region is open to the outside and sliding is used to align to the membrane layer. In this case the device can be used in a semiautomated manner, where the device is disassembled and the membrane layer is removed and processed in similar fashion to conventional blotting membranes (such as washing in a tray and/or exposing to film for detection). This semi-automated mode can be performed with a two-layer version of the device as described, or with devices having more layers, since the layers can be easily disassembled post process.

Devices can have different forms and shapes (e.g., rectangular, square, or round) as long as at least one layer can be slid relative to one or more other layers to align channels, membranes, and/or ports.

In some embodiments, a stain-free reagent such as trichlorethanol (TCE) is incorporated into the gel matrix, allowing for detection of protein analytes during the separation step upon exposure to UV light. Such detection can provide early confirmation that the sample has separated satisfactorily. The stain-free reagent also allows for the tracking of transfer efficiency and for normalization of sample loads, as described for Bio-Rad's V3 workflow.

In some embodiments, the membrane is replaced by a porous support and the transfer slit is used to introduce stains (for example, Coomassie, Flamingo, SYPRO Ruby, or Colloidal Gold) to detect proteins or nucleic acids rapidly within the separation medium. In other embodiments, separated molecules can be detected directly using their inherent absorbance by scanning the channel length (for example, using UV light).

In still other embodiments the sample ports and channel shape upstream of the separation channel are designed to allow for the concentration of sample, for example by isotachophoresis, prior to separation. One such design is a progressive tapering of the channel.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded.

All documents (for example, patents, patent applications, books, journal articles, or other publications) cited herein are incorporated by reference in their entirety and for all purposes, to the same extent as if each individual document was specifically and individually indicated to be incorporated by reference in its entirety for all purposes. To the extent such documents incorporated by reference contradict the disclosure contained in the specification, the specification is intended to supersede and/or take precedence over any contradictory material.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

What is claimed is:

1. A device for separating and detecting analytes of a biological sample, the device comprising:
    a first solid substrate comprising a first surface, a plurality of α first half-spaces, and a plurality of β first half-spaces, the α and β first half-spaces disposed in the first surface in a repeating array, such that each α first half-space is adjacent to a β first half-space;
    a first capture agent disposed on the first surface within the α first half-spaces;
    a second solid substrate comprising a second surface, a plurality of α second half-spaces and a plurality of β second half-spaces, the α and β second half-spaces disposed in the second surface in a repeating array, such that each α second half-space is adjacent to a β second half-space;
    a second capture agent disposed on the second surface within the α second half-spaces; and
    a plurality of access ports;
    wherein:
    the first surface and second surface contact each other at an interface;
    the half-spaces are configured to contain fluids or separation media;
    the first half-spaces are complementary in shape to the second half-spaces, such that, when one first half-space is aligned with one second half-space, the one first half-space and the one second half-space together form a channel;
    the first solid substrate is configured to alternatively occupy two positions relative to the second solid substrate, the two positions being:
    an α-α position, such that the α first half-spaces are aligned with α second half-spaces to form separation channels; and
    an α-β position, such that the α first half-spaces are aligned with β second half-spaces to form α-β channels, and the β first half-spaces are aligned with α second half-spaces to form β-α channels, the α-β and β-α channels being detection channels;
    the first solid substrate is configured to slide past the second solid substrate along the interface; and
    the access ports are configured to provide access to the separation channels and the detection channels from space outside the device.

2. The device of claim 1, wherein the first capture agent or the second capture agent is a crosslinker.

3. The device of claim 1, wherein:
    the first capture agent is attached to the first surface through a linker, or
    the second capture agent is attached to the second surface through a linker.

4. The device of claim 1, wherein the first surface and the second surface are configured to contact each other with a fluid-tight seal, such that a fluid contained in an α first half-space, a β first half-space, an α second half-space, a β second half-space, a separation channel, or a detection channel cannot escape from said half-space or channel through the interface.

5. The device of claim 1, wherein the access ports comprise through-holes in the first solid substrate, and at least one through-hole provides a passage between each α first half-space and space outside the first solid substrate.

6. The device of claim 5, wherein a vacuum source or pressure source is coupled to at least one of the through-holes.

7. The device of claim 5, wherein an electrode is disposed in at least one of the through-holes.

8. The device of claim 5, wherein at least one through-hole provides a passage between each β first half-space and space outside the first solid substrate.

9. The device of claim 1, wherein the first solid substrate or the second solid substrate is transparent, in whole or in part, to UV and/or visible light, and the device further comprises a UV and/or visible light source configured to direct light into the separation channels or the detection channels.

10. The device of claim 1, wherein
the first half-spaces and second half-spaces are linear,
the α first half-spaces and the β first half-spaces are parallel to each other in the first surface,
each first half-space is disposed along a separation axis, such that when one first half-space is aligned with one second half-space, the one first half-space and the one second half-space are in fluidic contact along the separation axis, and
the first solid substrate and second solid substrate are configured to slide past each other such that the first solid substrate or the second solid substrate moves in a direction orthogonal to the separation axis.

11. The device of claim 1, wherein the depth of at least one β first half-space is less than the depth of at least one α first half-space, and the depth of at least one β second half-space is less than the depth of at least one α second half-space.

12. The device of claim 1, wherein the β first half-spaces and the β second half-spaces have depths of about zero.

13. A system for automatically separating and immobilizing analytes of a biological sample, the system comprising:
the device of claim 1, and
a motor configured to drive the sliding movement of the first solid substrate past the second solid substrate, from the α-α position to the α-β position.

14. The system of claim 13, further comprising a detector configured to detect light emitted from the detection channels.

15. A method of separating and detecting analytes of a biological sample using the device of claim 1, the method comprising:
(a) separating analytes of the biological sample in a separation medium, wherein the separation medium is contained in a separation channel, and the separation channel is formed from an α first half-space aligned with an α second half-space;
(b) immobilizing the analytes within the separation channel, using the first capture agent and the second capture agent;
(c) sliding the first solid substrate past the second solid substrate, from the α-α position to the α-β position, thereby disrupting the separation channel and forming two detection channels, wherein one detection channel is an α-β channel formed from the α first half-space and the other detection channel is a β-α channel formed from the α second half-space; and
(d) detecting the immobilized analytes in at least one of the two detection channels formed in step (c).

16. The method of claim 15, wherein separating the analytes comprises performing electrophoresis, electroosmosis, or isoelectric focusing.

17. The method of claim 15, wherein the first capture agent or the second capture agent is a crosslinker, and immobilizing the analytes comprises crosslinking the analytes to the first surface or the second surface.

18. The method of claim 17, wherein the crosslinking is effected by exposing the separation channel to UV light.

19. The method of claim 15, further comprising introducing a detection medium into the separation channel or the detection channels, wherein the detection medium comprises a binding partner for one or more analytes, and the binding partner is a protein or nucleic acid.

20. The method of claim 2, wherein the crosslinker is benzophenone.

* * * * *